United States Patent [19]

Keil et al.

[11] Patent Number: 5,001,261
[45] Date of Patent: Mar. 19, 1991

[54] CYCLOHEXENONE DERIVATIVES AND THEIR USE FOR CONTROLLING UNDESIRABLE PLANT GROWTH

[75] Inventors: Michael Keil, Freinsheim; Rainer Becker, Bad Duerkheim; Dieter Jahn, Edingen-Neckarhausen; Norbert Goetz, Worms; Ulrich Schirmer, Heidelberg; Bruno Wuerzer, Otterstadt, all of Fed. Rep. of Germany

[73] Assignee: BASF Aktiengesellschaft, Ludwigshafen, Fed. Rep. of Germany

[21] Appl. No.: 185,233

[22] Filed: Apr. 18, 1988

Related U.S. Application Data

[63] Continuation of Ser. No. 692,622, Jan. 18, 1985, abandoned, which is a continuation-in-part of Ser. No. 658,433, Oct. 5, 1984, abandoned.

[30] Foreign Application Priority Data

Oct. 6, 1983 [DE] Fed. Rep. of Germany ....... 3336354

[51] Int. Cl.$^5$ ............................................. C07C 249/00
[52] U.S. Cl. .................................... 564/256; 564/51; 564/79; 564/170; 564/176; 564/189; 564/201; 564/221; 560/13; 560/27; 560/35; 71/100; 71/103; 71/105; 71/107; 71/111; 71/118; 71/120; 71/121

[58] Field of Search ................. 564/256, 51, 79, 170, 564/176, 189, 201, 221; 71/100, 103, 105, 107, 111, 118, 120, 121

[56] References Cited

FOREIGN PATENT DOCUMENTS

| 82694A2 | 7/1983 | European Pat. Off. . |
| 85529A2 | 8/1983 | European Pat. Off. . |
| 95330A1 | 11/1983 | European Pat. Off. . |
| 3248554 | 7/1983 | Fed. Rep. of Germany . |
| 1461170 | 1/1977 | United Kingdom . |
| 2116544 | 9/1983 | United Kingdom . |

Primary Examiner—Paul J. Killos
Attorney, Agent, or Firm—Keil & Weinkauf

[57] ABSTRACT

Cyclohexenone derivatives of the formula

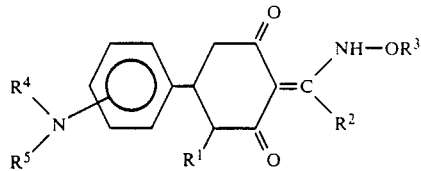

where $R^1$, $R^2$, $R^3$, $R^4$ and $R^5$ have the meanings given in the disclosure, and their use for controlling unwanted plant growth.

9 Claims, No Drawings

CYCLOHEXENONE DERIVATIVES AND THEIR USE FOR CONTROLLING UNDESIRABLE PLANT GROWTH

This application is a continuation application Ser. No. 06/692,622, filed on Jan. 18, 1985; abandoned which is a continuation-in-part application of Ser. No. 658,433 filed on Oct. 5, 1984, abandoned.

The present invention relates to cyclohexenone derivatives and to herbicides which contain these compounds as active ingredients.

It has been disclosed that cyclohexenone derivatives can be used for controlling undesirable grasses in broad-leaved crops (German Laid-Open Application DOS No. 2,439,104). Furthermore, German Laid-Open Application DOS No. 3,248,554 discloses that cyclohexen-1-one derivatives which carry a para-substituted phenyl radical in the 5-position control gramineous weeds in corn and wheat.

We have found that cyclohexenone derivatives of the formula

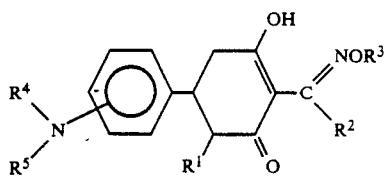

where $R^1$ is hydrogen, methoxycarbonyl, ethoxycarbonyl, methyl or cyano, $R^2$ is alkyl of 1 to 4 carbon atoms, $R^3$ is alkyl of 1 to 4 carbon atoms, alkenyl of 3 or 4 carbon atoms, haloalkenyl of 3 or 4 carbon atoms and 1 to 3 halogen substituents, or propargyl, $R^4$ is hydrogen or alkyl of 1 to 4 carbon atoms and, when the —$NR^4R^5$ group is in the meta-position, $R^5$ is hydrogen, alkyl, aliphatic acyl of 2 to 8 carbon atoms, formyl, cycloalkylcarbonyl of 4 to 7 carbon atoms, methoxyalkylcarbonyl, or benzoyl which is unsubstituted or substituted by nitro, halogen, alkyl or alkoxy, or is alkoxycarbonyl, benzyloxycarbonyl, phenoxycarbonyl, alkylthiocarbonyl, N,N-dialkylcarbamyl, N-alkylcarbamyl, N-cycloalkylcarbamyl where cycloalkyl is of 5 to 8 carbon atoms, N-alkoxy-N-alkylcarbamyl, or N-phenylcarbamyl which is unsubstituted or substituted by nitro, halogen, alkyl or alkoxy, or is N-alkylsulfamyl, N,N-dialkylsulfamyl, N-acyl-N-alkylsulfamyl where acyl is of 2 to 5 carbon atoms, or N-alkyl-N-methoxycarbonylsulfamyl, and, when the —$NR^4R^5$ group is in the para-position, $R^5$ is hydrogen, alkyl, cycloalkylcarbonyl where cycloalkyl is of 3 to 6 carbon atoms, methoxyalkylcarbonyl, or benzoyl which is unsubstituted or substituted by nitro, halogen, alkyl of 2 to 4 carbon atoms or alkoxy, or is benzyloxycarbonyl, phenoxycarbonyl, alkylthiocarbonyl, N-cycloalkylcarbamyl where cycloalkyl is of 5 to 8 carbon atoms, or N-phenylcarbamyl which is unsubstituted or substituted by nitro, halogen, alkyl or alkoxy, or is N-alkylsulfamyl, N,N-dialkylsulfamyl, N-acyl-N-alkylsulfamyl where acyl is of 2 to 5 carbon atoms or N-alkyl-N-methoxycarbonylsulfamyl, and salts of these compounds possess herbicidal activity.

The cyclohexenone derivatives of the formula I can occur in a plurality of forms, all of which are embraced by the claim:

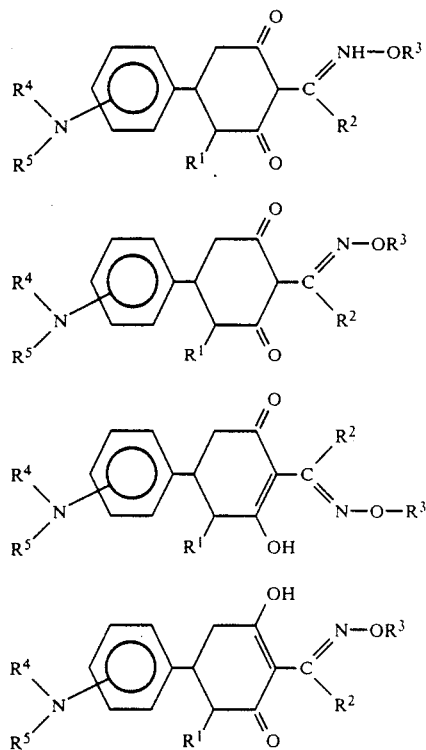

In formula I, $R^1$ is hydrogen, methoxycarbonyl, ethoxycarbonyl, methyl or cyano, $R^2$ is straight-chain or branched alkyl of 1 to 4 carbon atoms, i.e. methyl, ethyl, n-propyl, i-propyl, n-butyl, sec.-butyl, i-butyl or tert.-butyl, $R^3$ is propargyl, alkyl of 1 to 4 carbon atoms, alkenyl of 3 or 4 carbon atoms or haloalkenyl of 3 or 4 carbon atoms which can contain not more than 3 halogen substituents, preferably chloroalkenyl, e.g. methyl, ethyl, n-propyl, i-propyl, n-butyl, sec.-butyl, i-butyl, tert.-butyl, allyl, 1-chloroprop-1-en-3-yl, 2-chloroprop-1-en-3-yl, 1,3-dichloroprop-1-en-3-yl or 1,1,2-trichloroprop-1-en-3-yl, and $R^4$ is hydrogen or alkyl of 1 to 4 carbon atoms, i.e. methyl, ethyl, propyl, isopropyl, n-butyl, sec.-butyl, i-butyl or tert.-butyl.

The —$NR^4R^5$ group in formula I is in the meta- or para-position.

Where the —$NR^4R^5$ group is in the meta-position, $R^5$ in formula I is hydrogen, alkyl, aliphatic acyl of 2 to 8 carbon atoms, formyl, cycloalkylcarbonyl of 4 to 7 carbon atoms, methoxyalkylcarbonyl, or benzoyl which is unsubstituted or substituted by nitro, halogen, $C_1$-$C_4$-alkyl or $C_1$-$C_4$-alkoxy, or is alkoxycarbonyl, benzyloxycarbonyl, phenoxycarbonyl, alkylthiocarbonyl, N,N-dialkylcarbamyl, N-alkylcarbamyl, N-cycloalkylcarbamyl where cycloalkyl is of 5 to 8 carbon atoms, N-alkoxy-N-alkylcarbamyl, or N-phenylcarbamyl which is unsubstituted or substituted by nitro, halogen, alkyl or alkoxy, or is N-alkylsulfamyl, N,N-dialkylsulfamyl, N-acyl-N-alkylsulfamyl where acyl is of 2 to 5 carbon atoms or N-alkyl-N-methoxycarbonylsulfamyl.

Where the —$NR^4R^5$ group is in the para-position, $R^5$ in formula I is hydrogen, alkyl, cycloalkylcarbonyl of 4 to 7 carbon atoms, methoxyalkylcarbonyl, or benzoyl which is unsubstituted or substituted by nitro, halogen, alkyl of 2 to 4 carbon atoms or alkoxy of 1 to 4 carbon atoms, or is benzyloxycarbonyl, phenoxycarbonyl, alkylthiocarbonyl, N-cycloalkylcarbamyl where cycloalkyl is of 5 to 8 carbon atoms, or N-phenylcarbamyl which is unsubstituted or substituted by nitro, halogen, alkyl or alkoxy, or is N-alkylsulfamyl, N,N-dialkylsulfamyl, N-acyl-N-alkylsulfamyl where acyl is of 2 to 5 carbon atoms or N-alkyl-N-methoxycarbonylsulfamyl.

The alkyl groups $R^5$, and the alkyl and alkoxy groups in the radicals stated for $R^5$, can be straight-chain or branched and, unless stated otherwise, are of 1 to 4 carbon atoms, i.e. suitable alkyl or alkoxy radicals are methyl, ethyl, n-propyl, i-propyl, n-butyl, sec.-butyl, i-butyl, tert.-butyl, methoxy, ethoxy, n-propoxy, i-propoxy, n-butoxy, i-butoxy, sec.-butoxy and tert.-butoxy.

When the $-NR^4R^5$ groups are in the meta-position, $R^5$ is, for example, hydrogen, methyl, ethyl, acetyl, propionoyl, butylcarbonyl, formyl, cyclopropylcarbonyl, cyclopentylcarbonyl, cyclohexylcarbonyl, methoxy acetyl, 2-methoxypropionyl, 3-methoxypropionyl, benzoyl, 3-nitrobenzoyl, 2-chlorobenzoyl, 4-methylbenzoyl, 4-methoxybenzoyl, methoxycarbonyl, ethoxycarbonyl, benzyloxycarbonyl, phenoxycarbonyl, methylthiocarbonyl, ethylthiocarbonyl, isopropylthiocarbonyl, N,N-dimethylcarbamyl, N-methylcarbamyl, N-cyclohexylcarbamyl, N-(4-nitrophenyl)-carbamyl, N-(2-chlorophenyl)-carbamyl, N-(3-methylphenyl)-carbamyl, N-(3-methoxyphenyl)-carbamyl, N-methoxy-N-methylcarbamyl, N-methylsulfamyl, N,N-dimethylsulfamyl, N,N-diethylsulfamyl, N-acetyl-N-methylsulfamyl, N-butyryl-N-ethylsulfamyl, N-methoxycarbonyl-N-methylsulfamyl or N-isopropyl-N-methoxycarbonylsulfamyl.

When the $-NR^4R^5$ groups are in the para-position, $R^5$ is, for example, hydrogen, methyl, ethyl, cyclopropylcarbonyl, cyclopentylcarbonyl, cyclohexylcarbonyl, methoxyacetyl, 3-methoxypropionyl, 2-methoxypropionyl, benzoyl, 3-nitrobenzoyl, 2-chlorobenzoyl, 4-methoxybenzoyl, benzyloxycarbonyl, phenoxycarbonyl, methylthiocarbonyl, ethylthiocarbonyl, isopropylthiocarbonyl, N-cyclopentylcarbamyl, N-cyclohexylcarbamyl, N-(4-nitrophenyl)-carbamyl, N-(2-chlorophenyl)-carbamyl, N-(3-methylphenyl)-carbamyl, N-(3-methoxyphenyl)-carbamyl, N-methylsulfamyl, N,N-dimethylsulfamyl, N,N-diethylsulfamyl, N-acetyl-N-methylsulfamyl, N-butyryl-N-ethylsulfamyl, N-methoxycarbonyl-N-methylsulfamyl or N-isopropyl-N-methoxycarbonylsulfamyl.

Examples of suitable salts of the compounds of the formula I are the alkali metal salts, in particular the potassium and sodium salts, the alkaline earth metal salts, in particular calcium, magnesium and barium salts, manganese salts, copper salts, zinc salts and iron salts, and ammonium and phosphonium salts, for example alkylammonium, dialkylammonium, trialkylammonium, tetraalkylammonium, benzyltrialkylammonium, triphenylphosphonium, trialkylsulfonium and trialkylsulfoxonium salts.

Cyclohexenone derivatives of the formula

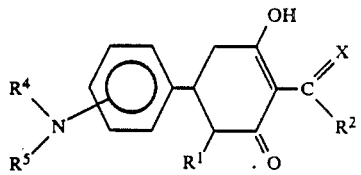

where the $-NR^4R^5$ group is in the meta- or para-position, X is oxygen or $-NH-$ and $R^1$, $R^2$, $R^4$ and $R^5$ have the above meanings, are novel and are essential intermediates for the herbicidal active ingredients of the formula I. In particular, the compounds of the formula II, where $R^1$, $R^4$ and $R^5$ are each hydrogen, $R^2$ is alkyl of 1 to 4 carbon atoms and X is NH, serve as principal intermediates for herbicidal active ingredients of the formula I.

The herbicidal cyclohexenone derivatives of the formula I can be obtained by reacting a compound of the formula II with a hydroxylamine derivative $R^3O-NH_3Y$ in which $R^3$ has the above meanings and Y is an anion.

The reaction is advantageously carried out in the heterogeneous phase in an inert diluent at from 0° to 80° C. or from 0° C. to the boiling point of the reaction mixture, in the presence of a base. Examples of suitable bases are carbonates, bicarbonates, acetates, alcoholates, hydroxides and oxides of alkali metals and alkaline earth metals, in particular of sodium, potassium, magnesium and calcium. Organic bases, such as pyridine or tertiary amines, can also be used.

The reaction proceeds particularly well at a pH of from 2 to 9, in particular from 4.5 to 5.5, the pH advantageously being adjusted by the addition of acetates, for example alkali metal acetates, in particular sodium acetate or potassium acetate, or a mixture of the two salts. Alkali metal acetates are added, for example, in amounts of from 0.5 to 2 moles per mole of the ammonium compound of the formula $R^3O-NH_3Y$.

Examples of suitable solvents are dimethylsulfoxide, alcohols, such as methanol, ethanol, isopropanol, benzene, hydrocarbons and chlorohydrocarbons, such as chloroform, dichloroethane, hexane or cyclohexane, esters, such as ethyl acetate, and ethers, such as dioxane or tetrahydrofuran.

The reaction is complete after a few hours, and the product can then be isolated by evaporating down the mixture, adding water, extracting with a non-polar solvent, such as methylene chloride, and distilling off the solvent under reduced pressure.

The compounds of the formula I can also be obtained by reacting a compound of the formula II with a hydroxylamine of the formula $R^3O-NH_2$, where $R^3$ has the above meanings, in an inert diluent at from 0° C. to the boiling point of the reaction mixture, in particular from 15° to 70° C. If necessary, the hydroxylamine can be employed in the form of an aqueous solution.

In the reaction of a compound of the formula II where X is $-NH-$ the reaction is completed by using a 1.5–2 molar excess of free O-alkylhydroxylamine, whereas in the conversion of compounds of the formula II where X is oxygen, a 1–1.1 molar amount is sufficient.

Examples of suitable solvents for this reaction are alcohols, such as methanol, ethanol, isopropanol, or cyclohexanol, hydrocarbons and chlorohydrocarbons, such as hexane, cyclohexane, methylene chloride, toluene or dichloroethane, esters, such as ethyl acetate, nitriles, such as acetonitrile, and cyclic ethers, such as tetrahydrofuran.

The alkali metal salts of the compounds of the formula I can be obtained by treating these compounds with sodium hydroxide or potassium hydroxide in aqueous solution or in an organic solvent, such as methanol, ethanol or acetone. A sodium alcoholate or a potassium alcoholate may also be used as the base.

The other metal salts, e.g. the manganese, copper, zinc, iron, calcium, magnesium and barium salts, can be prepared from the sodium salts by reaction with the corresponding metal chlorides in aqueous solution. Ammonium, phosphonium, sulfonium and sulfoxonium salts can be prepared by reacting compounds of the formula I with ammonium, phosphonium, sulfonium or sulfoxonium hydroxides, if necessary in aqueous solution.

The compounds of the formula II where X is oxygen can be prepared from a cyclohexane-1,3-dione of the formula (VII)

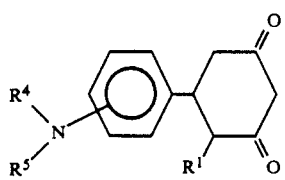

by a conventional method (Tetrahedron Lett. 29 (1975), 2491).

It is also possible to prepare compounds of the formula II where X is oxygen via the intermediate stage of the enol-esters, which are obtained, possibly as isomer mixtures, in the acylation of compounds of the formula VII, and undergo rearrangement in the presence of imidazole or pyridine derivatives (Japanese Preliminary Published Application No. 79/063052).

The compounds of the formula VII are in turn obtained by conventional methods, as can be seen from the equations below:

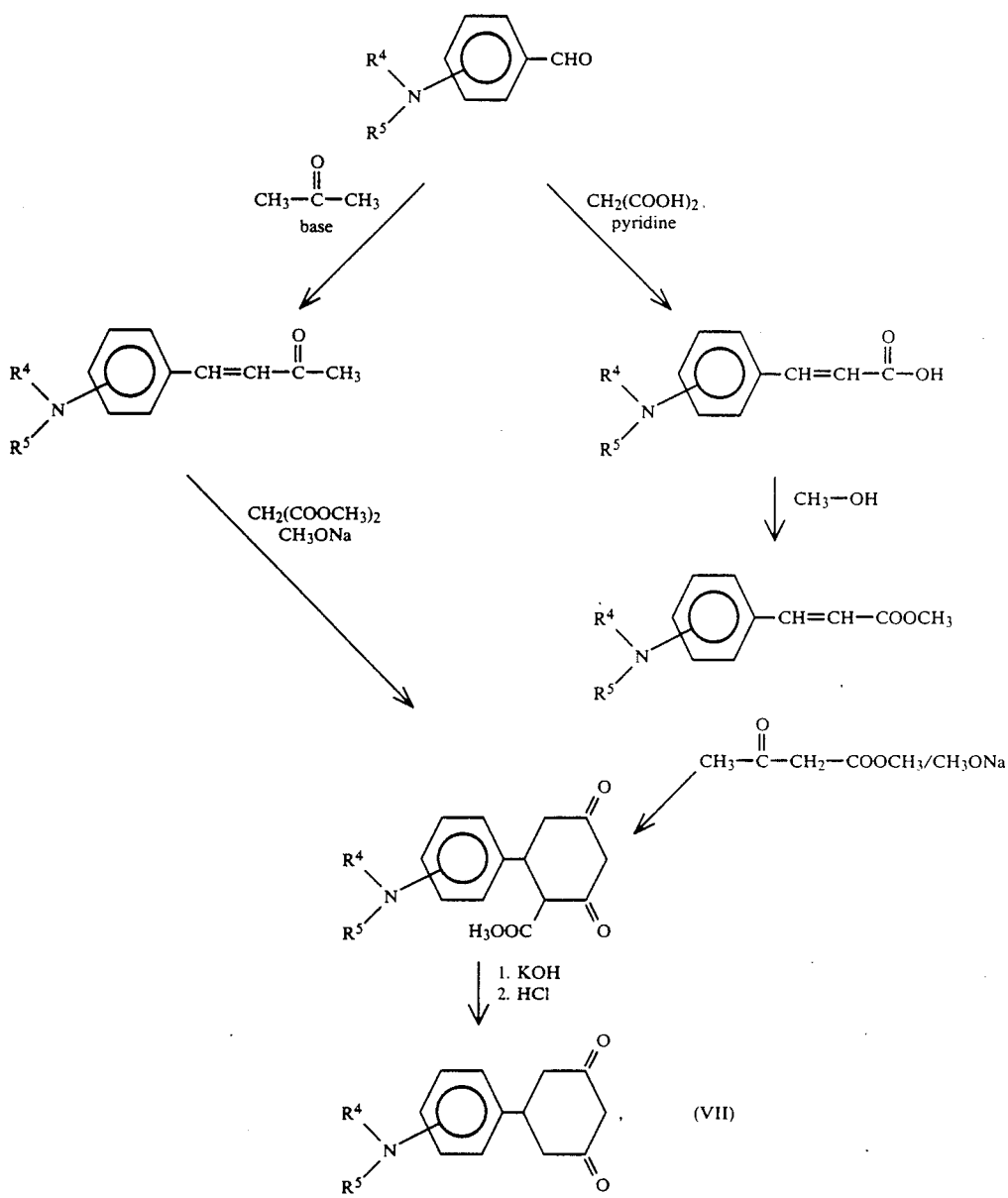

The cyclohexenone derivatives of the formulae

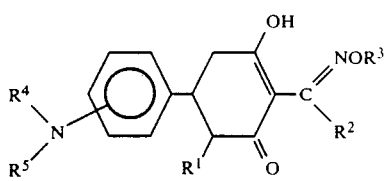

-continued

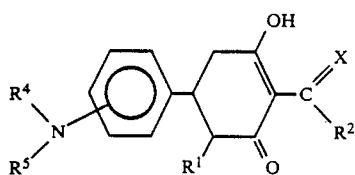

where $R^1$ and $R^4$ are each hydrogen, $R^2$ is alkyl of 1 to 4 carbon atoms, X is oxygen or —NH— and, where the —NR$^4$R$^5$ group is in the meta-position, $R^5$ is aliphatic acyl of 2 to 8 carbon atoms, formyl, cycloalkylcarbonyl of 4 to 7 carbon atoms, methoxyalkylcarbonyl, or benzoyl which is unsubstituted or substituted by nitro, halogen, alkyl or alkoxy, or is alkoxycarbonyl, benzyloxycarbonyl, phenoxycarbonyl, alkylthiocarbonyl, N,N-dialkylcarbamyl, N-alkoxy-N-alkylcarbamyl, N-alkylsulfamyl, N,N-dialkylsulfamyl, N-acyl-N-alkylsulfamyl where acyl is of 2 to 5 carbon atoms or N-alkyl-N-methoxycarbonylsulfamyl, or, where the —NR$^4$R$^5$ group is in the para-position, $R^5$ is cycloalkylcarbonyl of 4 to 7 carbon atoms, methoxyalkylcarbonyl, or benzoyl which is unsubstituted or substituted by nitro, halogen, alkyl or alkoxy, or is benzyloxycarbonyl, phenoxycarbonyl, alkylthiocarbonyl, N-alkylsulfamyl, N,N-dialkylsulfamyl, N-acyl-N-alkylsulfamyl where acyl is of 2 to 5 carbon atoms or N-alkyl-N-methoxycarbonylsulfamyl, can be obtained by reacting a compound of the formula I or II, where $R^5$ is hydrogen, with an electrophilic reagent $R^5$-Y (III) in which $R^5$ has the above meanings and Y is a leaving group, such as chlorine, bromine or carboxylate.

The reaction is carried out in the presence or absence of an inert organic solvent, examples of suitable solvents being hydrocarbons, such as naphtha, gasoline, toluene, pentane or cyclohexane, halohydrocarbons, such as methylene chloride, chloroform, dichloroethane, chlorobenzene or o-, m- or p-dichlorobenzene, nitrohydrocarbons, such as nitrobenzene or nitromethane, nitriles, such as acetonitrile, butyronitrile or benzonitrile, ethers, such as diethyl ether, tetrahydrofuran or dioxane, esters, such as ethyl acetate or methyl propionate, ketones, such as acetone or methyl ethyl ketone, and amides, such as dimethylformamide or formamide, as well as mixtures of these. The amount of solvent is from 100 to 5000% by weight, based on the aniline derivative employed.

Advantageously, the reaction is carried out in the presence of a conventional acid acceptor. Suitable acid acceptors are alkali metal hydroxides, alkali metal carbonates, alkali metal bicarbonates, alkaline earth metal hydroxides, alkaline earth metal carbonates, alkaline earth metal bicarbonates, alkaline earth metal oxides and amines, e.g. sodium bicarbonate, potassium carbonate, triethylamine, tributylamine, pyridine, N,N-dimethylaniline, N,N-dimethyl-N-cyclohexylamine or quinoline. The amount of acid acceptor is from 1 to 4 moles per mole of aniline derivative employed.

The reaction temperature is from $-20°$ to $+150°$ C., preferably from 20° to 80° C. The electrophilic reagents $R^5$Y and the compounds of the formula I or II which are used as starting materials are preferably employed in equimolar amounts.

Examples of compounds of the formula $R^5$Y are carboxylic acid halides, carboxylic acid anhydrides, chloroformates, alkylthiocarbonyl chlorides, N,N-dialkylcarbamyl chlorides, N-alkoxy-N-alkylcarbamyl chlorides, N-alkylsulfamyl chlorides and N-acyl-N-alkylsulfamyl chlorides, such as carboxylic acid halides of the formula $$R^7-CO-Hal,$$

where $R^7$ is alkyl of 1 to 7 carbon atoms, cycloalkyl of 3 to 5 carbon atoms, methoxyalkyl of 2 to 4 carbon atoms, or phenyl which is unsubstituted or substituted by nitro, halogen, alkyl of 1 to 4 carbon atoms or alkoxy of 1 to 3 carbon atoms, formic acetic anhydride of the formula

chloroformates of the formula $$R^8O-CO-Hal,$$

where $R^8$ is alkyl of 1 to 4 carbon atoms, benzyl or phenyl, alkylthiocarbonyl chlorides of the formula $$R^9S-CO-Cl,$$

where $R^9$ is alkyl of 1 to 4 carbon atoms, N,N-dialkylaminocarbamyl chlorides of the formula

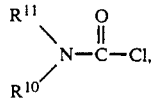

where $R^{10}$ and $R^{11}$ are each alkyl of 1 to 4 carbon atoms, N-alkoxy-N-alkylcarbamyl chlorides of the formula

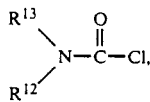

where $R^{12}$ is alkyl of 1 to 4 carbon atoms and $R^{13}$ is alkoxy of 1 to 4 carbon atoms, and sulfamyl chlorides of the formula

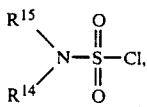

where $R^{14}$ is alkyl of 1 to 4 carbon atoms and $R^{15}$ is hydrogen, alkyl of 1 to 4 carbon atoms, acyl of 2 to 5 carbon atoms or methoxycarbonyl.

The cyclohexenone derivatives of the formulae:

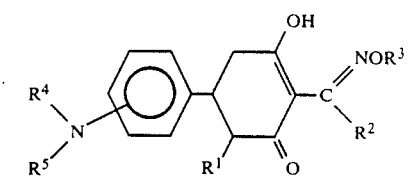

and

-continued

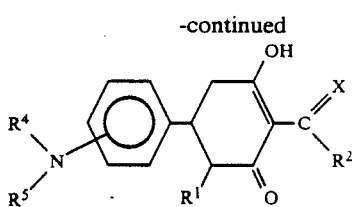
(II)

where $R^1$ and $R^4$ are each hydrogen, $R^2$ is alkyl of 1 to 4 carbon atoms, X is oxygen or —NH— and, where the —$NR^4R^5$ group is in the meta-position, $R^5$ is N-alkylcarbamyl, N-cycloalkylcarbamyl where cycloalkyl is of 5 to 8 carbon atoms, or N-phenylcarbamyl which is unsubstituted or substituted by nitro, halogen, alkyl or alkoxy, or, where the —$NR^4R^5$ group is in the para-position, $R^5$ is N-cycloalkylcarbamyl where cycloalkyl is of 5 to 8 carbon atoms, or N-phenylcarbamyl which is unsubstituted or substituted by nitro, halogen, alkyl or alkoxy, are furthermore obtained by reacting the corresponding amino derivatives with an isocyanate of the formula

$R^6$—NCO    (IV), where $R^6$ has the meanings stated above for $R^5$.

The reaction is carried out in the presence or absence of a catalyst conventionally used for isocyanate reactions, for example a tertiary amine, such as triethylamine or 1,4-diazabicyclo-[2.2.2]octane, nitrogen-containing heterocyclic compounds, such as pyridine or 1,2-dimethylimidazole, or organic tin compounds, such as dibutyl-tin diacetate or dimethyl-tin dichloride, and in the presence or absence of a solvent which is inert under the reaction conditions, for example a hydrocarbon, such as naphtha, gasoline, toluene, pentane or cyclohexane, a halohydrocarbon, such as methylene chloride, chloroform, dichloroethane, chlorobenzene or o-, m- or p-dichlorobenzene, a nitrohydrocarbon, such as nitrobenzene or nitromethane, a nitrile, such as acetonitrile, butyronitrile or benzonitrile, an ether, such as diethyl ether, tetrahydrofuran or dioxane, an ester, such as ethyl acetate or methyl propionate, a ketone, such as acetone or methyl ethyl ketone, or an amide, such as dimethylformamide or formamide (Houben-Weyl, Methoden der organ. Chemie, 4th Edition, 1952, Vol. VIII, page 132, Georg Thieme-Verlag, Stuttgart).

The amount of catalyst is from 0.1 to 5 mole %, based on the aniline derivative employed, the amount of solvent is from 100 to 10,000% by weight, and the reaction temperature can be from −20° to 150° C., preferably from 0° to 100° C.

A compound of the formula

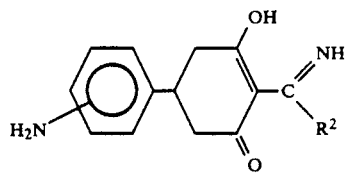
(IIb)

in which the amino group is in the meta- or para-position and $R^2$ is alkyl of 1 to 4 carbon atoms, is prepared by reducing a compound of the formula

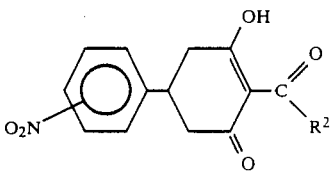
(VI)

in which the nitro group is in the meta- or para-position and $R^2$ is alkyl of 1 to 4 carbon atoms, with an iron(II) salt in the presence of ammonia, water and an organic solvent.

Because the compounds of the formula VI have a keto-enol structure, some of the well known methods for preparing aromatic amines by reduction of nitro compounds (Houben-Weyl, Methoden der organischen Chemie, 4th Edition, 1957, Vols. 11/1, page 360, Georg Thieme Verlag, Stuttgart), such as reduction with iron and mineral acids, reduction with sulfides and sulfites or reduction with tin, zinc or aluminum, are unsuitable. In contrast, in the reduction of VI with iron(II) salts in the presence of aqueous ammonia solution to give IIb, the expected intermolecular condensation reactions are avoided owing to the alkaline medium on the one hand and the simultaneous imine formation in the 2-acyl radical on the other hand. The imine formation observed here, which takes place when compounds containing nitro groups in the presence of carbonyl groups are reduced by means of iron(II) salts and ammonia, has not been described in the literature to date. According to the literature, even aldehyde groups remain unaffected under these reaction conditions and do not form an imine (J. Org. Chem. 16 (1951), 1736; J. Amer. Chem. Soc. 51 (1929), 532 and Org. Synth. 28 (1948), 11).

Suitable iron salts are iron(II) sulfate, iron(II) chloride and ammonium ferrous sulfate, iron(II) sulfate preferably being used.

The reaction temperature is from 0° to 100° C., preferably from 50° to 100° C.

Suitable solvents for the nitro compounds of the formula VI which are employed are alcohols, e.g. methanol, ethanol, propanol, isopropanol, n-butanol or isobutanol, ketones, e.g. acetone or methyl ethyl ketone, and amides, e.g. dimethylformamide or formamide, as well as mixtures of these. The compounds of the formula IIb, which are obtained in crystalline form, are stable in dilute mineral acids and in a strongly alkaline medium and are useful intermediates for the cyclohexenone derivatives of the formula I where $R^1$ and $R^4$ are each hydrogen; these can be prepared either via reaction at the amino group followed by conversion of the product to the oxime-ether, or via formation of the oxime-ether followed by reaction at the amino group:

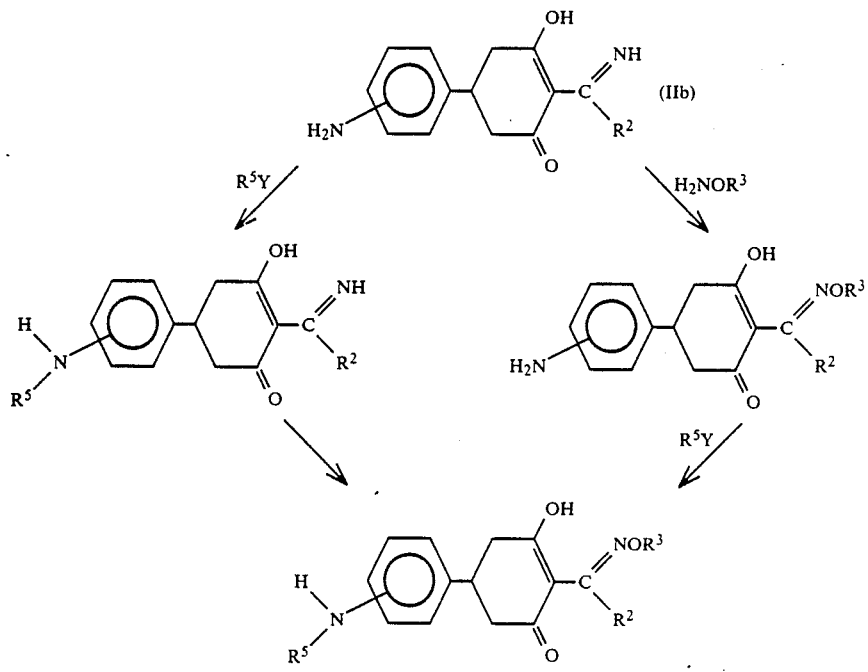

The preparation of compounds of the formula

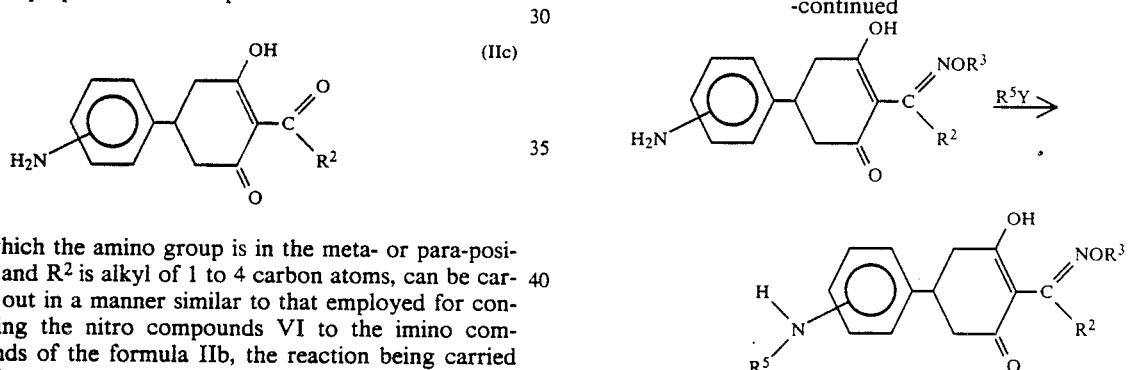

in which the amino group is in the meta- or para-position and $R^2$ is alkyl of 1 to 4 carbon atoms, can be carried out in a manner similar to that employed for converting the nitro compounds VI to the imino compounds of the formula IIb, the reaction being carried out in dilute sodium hydroxide solution, instead of in ammonia solution, under otherwise identical conditions and using the same solvents.

In certain cases, the compounds of the formula IIc may also be obtained as sparingly soluble salt-like compounds of the formula IId:

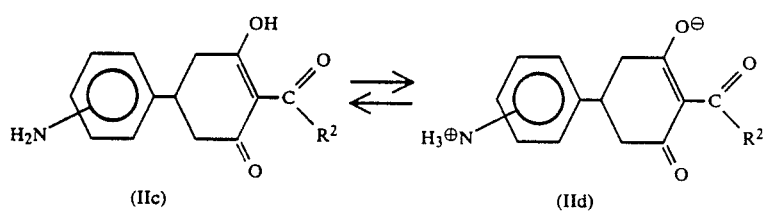

The compounds of the formula IIc or IId can also be used for the preparation of cyclohexenone derivatives of the formula I where $R^1$ and $R^4$ are each hydrogen.

Another method for the reduction of the meta- or para-nitro compounds of the formula VI to the corresponding amino compounds of the formula IIc is catalytic hydrogenation with hydrogen:

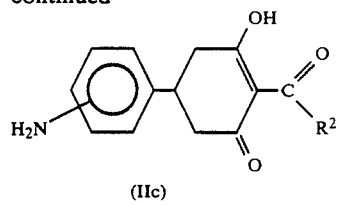

(IIc)

This procedure is carried out in the presence or absence of an inert solvent, e.g. tetrahydrofuran, dioxane, a $C_1$–$C_4$-alcohol, ethylene glycol monomethyl ether, ethylene glycol monoethyl ether, dimethylformamide, pyridine, ethyl acetate, acetone or water or a mixture of these, under from 1 to 5 bar, preferably under atmospheric pressure, with the addition of a conventional hydrogenation catalyst, e.g. palladium, platinum or nickel, at from 0° to 80° C., preferably at room temperature, and, necessarily, with addition of a base, such as aqueous sodium hydroxide solution, a tertiary amine or an inorganic carbonate or acetate.

Using this method, meta- and para-nitro-substituted oxime-ethers of the formula

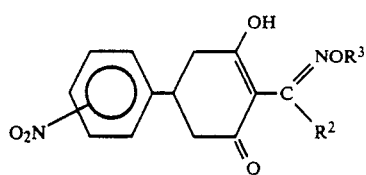

(V)

in which the nitro group is in the meta- or para-position and $R^2$ and $R^3$ are each alkyl of 1 to 4 carbon atoms, can be extremely easily converted to the amino derivatives of the formula Ib, which can then be reacted with an acid chloride or an isocyanate to give cyclohexenone derivatives of the formula I where $R^1$ and $R^4$ are each hydrogen, in accordance with the following equation:

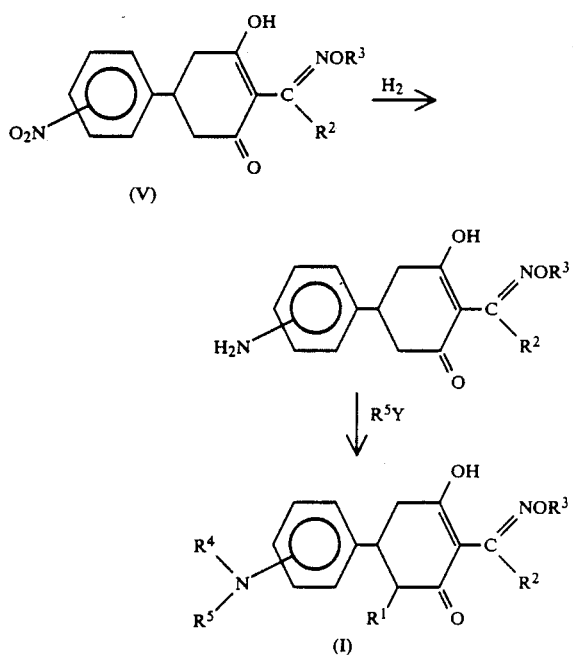

The Example which follows illustrates the preparation of the cyclohexenone derivatives of the formula II.

5-(4-Aminophenyl)-2-(1-imino-n-butyl)-3-hydroxycyclohex-2-en-1-one 52 parts by weight of 5-(4-nitrophenyl)-2-butyryl-cyclohexane-1,3-dione are dissolved in 1000 parts by volume of hot 75% strength ethanol, and the solution is introduced into a boiling solution of 400 parts of iron(II) sulfate heptahydrate in 1000 parts of water. Stirring is continued for a further 15 minutes after which the hot mixture is filtered and the residue is washed thoroughly with hot water. When the filtrates are left to stand, 37 parts of 5-(4-aminophenyl)-2-(1-imino-n-butyl)-3-hydroxycyclohex-2-en-1-one of melting point 133° C. crystallize out.

Calculated C 70.5, H 7.4, N 10.3. Found C 69.7, H 7.4, N 9.8.

The following cyclohexenone derivatives of the formula II can be prepared by a similar method:

| $-N\overset{R^4}{\underset{R^5}{\diagdown}}$ $R^5$ | $R^1$ | $R^2$ | X | Mp. [°C.] |
|---|---|---|---|---|
| 3-dimethylamino | H | n-$C_3H_7$ | O | |
| 3-methoxycarbonylamido | H | n-$C_3H_7$ | O | 110 |
| 4-methylcarbamyl | H | n-$C_3H_7$ | NH | >200 |
| 4-phenylcarbamyl | H | n-$C_3H_7$ | O | >200 |
| cyclohexylcarbamyl | H | n-$C_3H_7$ | O | >200 |
| 4-benzoyl | $COOCH_3$ | n-$C_3H_7$ | O | 108–110 |
| 4-benzoyl | H | n-$C_3H_7$ | O | 160–162 |
| 3-benzoyl | H | n-$C_3H_7$ | NH | >200 |
| 4-methylbenzoyl | H | n-$C_3H_7$ | NH | >200 |
| 3-propionamido | H | n-$C_3H_7$ | NH | 193 |
| 3-amino | H | $C_2H_5$ | O | >200 |
| 3-amino | H | $C_2H_5$ | NH | |
| 4-amino | H | n-$C_3H_7$ | NH | 166 |

The Examples which follow illustrate the preparation of the cyclohexenone derivatives of the formula I. Parts by weight bear the same relation to parts by volume as that of the kilogram to the liter.

EXAMPLE 1

2-(1-Allyloximino-n-butyl)-5-(4-aminophenyl)-3-hydroxycyclohex-2-en-1-one 15 parts by weight of 5-(4-aminophenyl)-2-(1-aminobutylidene)-cyclohexane-1,3-dione, 13.3 parts by weight of 0-allylhydroxylamine hydrochloride, 10.2 parts by weight of sodium bicarbonate, 100 parts by volume of methanol and 50 parts by volume of methylene chloride are stirred for 16 hours at 25° C. and then evaporated down under reduced pressure at 30° C., and the residue is partitioned between water and methylene chloride. The methylene chloride phase is dried over sodium sulfate and evaporated down substantially. The addition of excess petroleum ether gives a pale yellow crystalline solid consisting of 12.5 parts by weight of 2-(1-allyloximinobutyl)-5-(4-aminophenyl)-3-hydroxycyclohex-2-en-1-one of melting point 92° C.

Calculated C 69.5, H 7.4, N 8.6. Found C 69.2, H 7.2, N 8.9.

EXAMPLE 2

5-(4-Aminophenyl)-2-(1-ethoximino-n-butyl)-3-hydroxycyclohex-2-en-1-one 5 parts by weight of 10% strength palladium on carbon are added to 43 parts by weight of 2-(1-ethoxyamino-n-butylidene)-5-(4-nitrophenyl)-cyclohexane- 1,3-dione in 1000 parts by volume of tetrahydrofuran, and the mixture is gassed with hydrogen at 30° C. until the theoretical amount of hydrogen has been taken up. The mixture is filtered and the filtrate is then evaporated down to give 37 parts by weight of pale brown crystals of 5-(4-aminophenyl)-2-(1-ethoximino-n-butyl)-3-hydroxycyclohex-2-en-1-one of melting point 118° C.

Calculated C 68.3, H 7.6, N 8.8. Found C 68.4, H 7.4, N 8.5.

EXAMPLE 3

5-(3-Benzamidophenyl)-2-(1-ethoximino-n-butyl)-3-hydroxycyclohex-2-en-1-one 4.3 parts by weight of 5-(3-benzamidophenyl)-2-(1-amino-n-butylidene)-cyclohexane-1,3-dione, 2.2 parts by weight of 0-ethylhydroxylammonium chloride, 1.9 parts by weight of sodium bicarbonate, 30 parts by volume of methanol and 20 parts of methylene chloride are stirred for 16 hours at room temperature, after which the mixture is evaporated to dryness under reduced pressure, and the residue is partitioned between water and methylene chloride. The methylene chloride phase is dried with sodium sulfate and evaporated down. 3.5 parts by weight of 5(3-benzamidophenyl)-2-(1-ethoximinobutyl)-3-hydroxycyclohex-2-en-1-one of melting point 62°-64° C. are obtained as a pale gray crystalline solid.

Calculated C 71.4, H 6.7, N 6.7. Found C 70.9, H 6.7, N 7.1.

5-[4-(4-Chlorobenzamido)-phenyl]-2-(1-ethoximino-n-butyl)-3-hydroxycyclohex-2-en-1-one 8 parts by weight of 5-(4-aminophenyl)-2-(1-ethoximino-n-butyl)-3-hydroxycyclohex-2-en-1-one are brought into solution with gentle heating, using 40 parts by volume of glacial acetic acid and 30 parts of saturated sodium acetate solution. 4.4 parts by weight of 4-chlorobenzoyl chloride are added dropwise, while cooling with ice, and the mixture is stirred for 2 hours at room temperature and then poured into water. The pale brown solid is filtered off, washed thoroughly with water and dried over sodium sulfate at 50° C. under reduced pressure. 10.2 parts by weight of 5-[4-4-chlorobenzamido)-phenyl]-2-(1-ethoximino-n-butyl)3-hydroxycyclohex-2-en-1-one of melting point 155°-157° C. are obtained as a slightly yellowish powder.

Calculated C 66.0, H 6.0, N 6.1. Found C 66.8, H 6.1, N 6.0.

EXAMPLE 5

2-(1-Ethoximino-n-propyl)-5-[3-3'-phenylureido)-phenyl]-3-hydroxycyclohex-2-en-1-one 1.96 parts by weight of phenyl isocyanate are added to 5 parts by weight of 5-(3-aminophenyl)-2-(1-ethoxyamino-n-propylidene)-cyclohexane-1,3-dione in 100 parts by volume of methylene chloride, and the solution is evaporated down after 16 hours. 6.7 parts by weight of 2-(1-ethoximino-n-propyl)-5-[3-(3'-phenylureido)-phenyl]-3-hydroxycyclohex-2-en-1-one of melting point 72°-75° C. are obtained.

Calculated C 68.4, H 6.5, N 10.0. Found C 68.3, H 6.3, N 10.1.

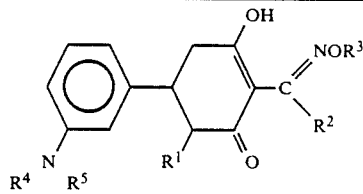

| Compound no. | $R^5$ | $R^1$ | $R^2$ | $R^3$ | $R^4$ | $n_D$/m.p. [°C.] |
|---|---|---|---|---|---|---|
| 1 | H | H | n-$C_3H_7$ | $C_2H_5$ | H | 129-130 |
| 2 | H | H | $C_2H_5$ | $C_2H_5$ | H | 1.5863 (24) |
| 3 | H | H | $C_2H_5$ | $CH_2$—CH=$CH_2$ | H | 1.5940 (27) |
| 4 | H | H | n-$C_3H_7$ | $CH_2$—CH=$CH_2$ | H | viscous oil |
| 5 | H | H | n-$C_3H_7$ | n-$C_3H_7$ | H | 1.5640 (20) |
| 6 | H | H | $C_2H_5$ | n-$C_3H_7$ | H | |
| 7 | methyl | H | n-$C_3H_7$ | $C_2H_5$ | $CH_3$ | 1.5705 (28) |
| 8 | methyl | H | n-$C_3H_7$ | $CH_2$—CH=$CH_2$ | $CH_3$ | |
| 9 | methyl | H | $C_2H_5$ | $CH_2$—CH=$CH_2$ | $CH_3$ | |
| 10 | acetyl | H | n-$C_3H_7$ | $C_2H_5$ | H | |
| 11 | acetyl | H | n-$C_3H_7$ | $CH_2$—CH=$CH_2$ | H | |
| 12 | acetyl | H | $C_2H_5$ | $CH_2$—CH=$CH_2$ | H | |
| 13 | acetyl | H | $C_2H_5$ | $C_2H_5$ | H | 108-114 |
| 14 | propionyl | H | n-$C_3H_7$ | $C_2H_5$ | H | oil |
| 15 | propionyl | H | n-$C_3H_7$ | $CH_2$—CH=$CH_2$ | H | |
| 16 | propionyl | H | $C_2H_5$ | $CH_2CH$=$CH_2$ | H | |
| 17 | propionyl | H | $C_2H_5$ | $C_2H_5$ | H | |
| 18 | butyryl | H | n-$C_3H_7$ | $C_2H_5$ | H | |
| 19 | butyryl | H | n-$C_3H_7$ | $CH_2$—CH=$CH_2$ | H | |
| 20 | butyryl | H | $C_2H_5$ | $CH_2$—CH=$CH_2$ | H | |
| 21 | butyryl | H | $C_2H_5$ | $C_2H_5$ | H | |
| 22 | heptanoyl | H | n-$C_3H_7$ | $C_2H_5$ | H | |
| 23 | heptanoyl | H | n-$C_3H_7$ | $CH_2$—CH=$CH_2$ | H | |
| 24 | heptanoyl | H | $C_2H_5$ | $CH_2$—CH=$CH_2$ | H | |
| 25 | heptanoyl | H | $C_2H_5$ | $C_2H_5$ | H | |
| 26 | formyl | H | n-$C_3H_7$ | $C_2H_5$ | H | |
| 27 | formyl | H | n-$C_3H_7$ | $CH_2$—CH=$CH_2$ | H | |
| 28 | formyl | H | $C_2H_5$ | $CH_2$—CH=$CH_2$ | H | |
| 29 | formyl | H | $C_2H_5$ | $C_2H_5$ | H | |

-continued

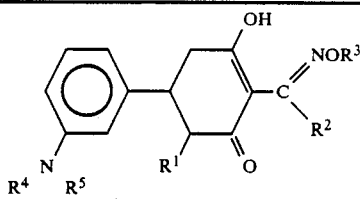

| Compound no. | R$^5$ | R$^1$ | R$^2$ | R$^3$ | R$^4$ | n$_D$/m.p. [°C.] |
|---|---|---|---|---|---|---|
| 30 | formyl | H | n-C$_3$H$_7$ | CH$_2$—CH=CHCl | H | |
| 31 | cyclopropylcarbonyl | H | n-C$_3$H$_7$ | C$_2$H$_5$ | H | |
| 32 | cyclopropylcarbonyl | H | n-C$_3$H$_7$ | CH$_2$—CH=CH$_2$ | H | |
| 33 | cyclopropylcarbonyl | H | C$_2$H$_5$ | CH$_2$—CH=CH$_2$ | H | |
| 34 | cyclopropylcarbonyl | H | C$_2$H$_5$ | C$_2$H$_5$ | H | |
| 35 | cyclopentylcarbonyl | H | n-C$_3$H$_7$ | C$_2$H$_5$ | H | |
| 36 | cyclopentylcarbonyl | H | n-C$_3$H$_7$ | CH$_2$—CH=CH$_2$ | H | |
| 37 | cyclopentylcarbonyl | H | C$_2$H$_5$ | CH$_2$CH=CH$_2$ | H | |
| 38 | cyclopentylcarbonyl | H | C$_2$H$_5$ | C$_2$H$_5$ | H | |
| 39 | cyclohexylcarbonyl | H | n-C$_3$H$_7$ | C$_2$H$_5$ | H | 110–115 |
| 40 | cyclohexylcarbonyl | H | n-C$_3$H$_7$ | CH$_2$—CH=CH$_2$ | H | |
| 41 | cyclohexylcarbonyl | H | C$_2$H$_5$ | CH$_2$CH=CH$_2$ | H | |
| 42 | cyclohexylcarbonyl | H | C$_2$H$_5$ | C$_2$H$_5$ | H | |
| 43 | methoxyacetyl | H | n-C$_3$H$_7$ | C$_2$H$_5$ | H | |
| 44 | methoxyacetyl | H | n-C$_3$H$_7$ | CH$_2$—CH=CH$_2$ | H | |
| 45 | methoxyacetyl | H | C$_2$H$_5$ | CH$_2$—CH=CH$_2$ | H | |
| 46 | methoxyacetyl | H | C$_2$H$_5$ | C$_2$H$_5$ | H | |
| 47 | 2-methoxypropionyl | H | n-C$_3$H$_7$ | C$_2$H$_5$ | H | |
| 48 | 2-methoxypropionyl | H | n-C$_3$H$_7$ | CH$_2$—CH=CH$_2$ | H | |
| 49 | 2-methoxypropionyl | H | C$_2$H$_5$ | CH$_2$—CH=CH$_2$ | H | |
| 50 | 2-methoxypropionyl | H | C$_2$H$_5$ | C$_2$H$_5$ | H | |
| 51 | 3-methoxypropionyl | H | n-C$_3$H$_7$ | C$_2$H$_5$ | H | |
| 52 | 3-methoxypropionyl | H | n-C$_3$H$_7$ | CH$_2$—CH=CH$_2$ | H | |
| 53 | 3-methoxypropionyl | H | C$_2$H$_5$ | CH$_2$—CH=CH$_2$ | H | |
| 54 | 3-methoxypropionyl | H | C$_2$H$_5$ | C$_2$H$_5$ | H | |
| 55 | benzoyl | H | n-C$_3$H$_7$ | C$_2$H$_5$ | H | 62–64 |
| 56 | benzoyl | H | n-C$_3$H$_7$ | CH$_2$—CH=CH$_2$ | H | |
| 57 | benzoyl | H | C$_2$H$_5$ | CH$_2$—CH=CH$_2$ | H | |
| 58 | benzoyl | H | C$_2$H$_5$ | C$_2$H$_5$ | H | |
| 59 | 3-nitrobenzoyl | H | n-C$_3$H$_7$ | C$_2$H$_5$ | H | |
| 60 | 3-nitrobenzoyl | H | n-C$_3$H$_7$ | CH$_2$—CH=CH$_2$ | H | |
| 61 | 3-nitrobenzoyl | H | C$_2$H$_5$ | CH$_2$—CH=CH$_2$ | H | |
| 62 | 3-nitrobenzoyl | H | C$_2$H$_5$ | C$_2$H$_5$ | H | 70–74 |
| 63 | 2-chlorobenzoyl | H | C$_2$H$_5$ | C$_2$H$_5$ | H | 74–77 |
| 64 | 2-chlorobenzoyl | H | n-C$_3$H$_7$ | CH$_2$—CH=CH$_2$ | H | 66–69 |
| 65 | 3-methoxybenzoyl | H | n-C$_3$H$_7$ | C$_2$H$_5$ | H | |
| 66 | 3-methoxybenzoyl | H | n-C$_3$H$_7$ | CH$_2$—CH=CH$_2$ | H | |
| 67 | 3-methoxybenzoyl | H | C$_2$H$_5$ | CH$_2$—CH=CH$_2$ | H | |
| 68 | 3-methoxybenzoyl | H | C$_2$H$_5$ | C$_2$H$_5$ | H | |
| 69 | 4-methylbenzoyl | H | n-C$_3$H$_7$ | C$_2$H$_5$ | H | 58–61 |
| 70 | 4-methylbenzoyl | H | n-C$_3$H$_7$ | CH$_2$—CH=CH$_2$ | H | |
| 71 | 4-methylbenzoyl | H | C$_2$H$_5$ | CH$_2$CH=CH$_2$ | H | |
| 72 | 4-methylbenzoyl | H | C$_2$H$_5$ | C$_2$H$_5$ | H | 72–76 |
| 73 | 4-n-propoxybenzoyl | H | n-C$_3$H$_7$ | C$_2$H$_5$ | H | |
| 74 | 4-t-butylbenzoyl | H | C$_2$H$_5$ | C$_2$H$_5$ | H | 91–92 |
| 75 | 4-nitrobenzoyl | H | n-C$_3$H$_7$ | C$_2$H$_5$ | H | 83–84 |
| 76 | 4-nitrobenzoyl | H | n-C$_3$H$_7$ | CH$_2$CH=CH$_2$ | H | |
| 77 | 4-nitrobenzoyl | H | C$_2$H$_5$ | CH$_2$—CH=CH$_2$ | H | |
| 78 | 4-nitrobenzoyl | H | C$_2$H$_5$ | C$_2$H$_5$ | H | 76–78 |
| 79 | 4-chlorobenzoyl | H | n-C$_3$H$_7$ | C$_2$H$_5$ | H | 107–110 |
| 80 | 4-chlorobenzoyl | H | n-C$_3$H$_7$ | CH$_2$—CH=CH$_2$ | H | |
| 81 | 4-chlorobenzoyl | H | C$_2$H$_5$ | CH$_2$—CH=CH$_2$ | H | |
| 82 | 4-chlorobenzoyl | H | C$_2$H$_5$ | C$_2$H$_5$ | H | |
| 83 | 4-methoxybenzoyl | H | n-C$_3$H$_7$ | C$_2$H$_5$ | H | |
| 84 | 4-methoxybenzoyl | H | n-C$_3$H$_7$ | CH$_2$—CH=CH$_2$ | H | |
| 85 | 4-methoxybenzoyl | H | C$_2$H$_5$ | CH$_2$—CH=CH$_2$ | H | 55–58 |
| 86 | 4-methoxybenzoyl | H | C$_2$H$_5$ | C$_2$H$_5$ | H | 68–71 |
| 87 | methoxycarbonyl | H | n-C$_3$H$_7$ | C$_2$H$_5$ | H | 136–143 |
| 88 | methoxycarbonyl | H | n-C$_3$H$_7$ | CH$_2$—CH=CH$_2$ | H | |
| 89 | methoxycarbonyl | H | C$_2$H$_5$ | CH$_2$—CH=CH$_2$ | H | |
| 90 | methoxycarbonyl | H | C$_2$H$_5$ | C$_2$H$_5$ | H | |
| 91 | ethoxycarbonyl | H | n-C$_3$H$_7$ | C$_2$H$_5$ | H | |
| 92 | ethoxycarbonyl | H | n-C$_3$H$_7$ | CH$_2$—CH=CH$_2$ | H | |
| 93 | ethoxycarbonyl | H | C$_2$H$_5$ | CH$_2$—CH=CH$_2$ | H | |
| 94 | ethoxycarbonyl | H | C$_2$H$_5$ | C$_2$H$_5$ | H | |
| 95 | n-butoxycarbonyl | H | n-C$_3$H$_7$ | C$_2$H$_5$ | H | |
| 96 | benzyloxycarbonyl | H | n-C$_3$H$_7$ | C$_2$H$_5$ | H | |
| 97 | benzyloxycarbonyl | H | n-C$_3$H$_7$ | CH$_2$—CH=CH$_2$ | H | |
| 98 | benzyloxycarbonyl | H | C$_2$H$_5$ | CH$_2$CH=CH$_2$ | H | |
| 99 | benzyloxycarbonyl | H | C$_2$H$_5$ | C$_2$H$_5$ | H | |
| 100 | phenoxycarbonyl | H | n-C$_3$H$_7$ | C$_2$H$_5$ | H | |

-continued

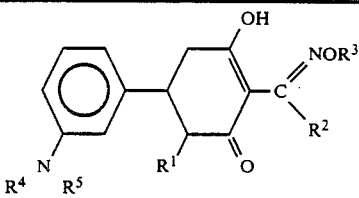

| Compound no. | R⁵ | R¹ | R² | R³ | R⁴ | $n_D$/m.p. [°C.] |
|---|---|---|---|---|---|---|
| 101 | phenoxycarbonyl | H | n-$C_3H_7$ | $CH_2-CH=CH_2$ | H | |
| 102 | phenoxycarbonyl | H | $C_2H_5$ | $CH_2-CH=CH_2$ | H | |
| 103 | phenoxycarbonyl | H | $C_2H_5$ | $C_2H_5$ | H | |
| 104 | methylthiocarbonyl | H | n-$C_3H_7$ | $C_2H_5$ | H | |
| 105 | methylthiocarbonyl | H | n-$C_3H_7$ | $CH_2-CH=CH_2$ | H | |
| 106 | methylthiocarbonyl | H | $C_2H_5$ | $CH_2-CH=CH_2$ | H | |
| 107 | methylthiocarbonyl | H | $C_2H_5$ | $C_2H_5$ | H | 84–86 |
| 108 | ethylthiocarbonyl | H | n-$C_3H_7$ | $C_2H_5$ | H | |
| 109 | ethylthiocarbonyl | H | n-$C_3H_7$ | $CH_2-CH=CH_2$ | H | |
| 110 | ethylthiocarbonyl | H | $C_2H_5$ | $CH_2-CH=CH_2$ | H | |
| 111 | ethylthiocarbonyl | H | $C_2H_5$ | $C_2H_5$ | H | |
| 112 | isopropylthiocarbonyl | H | n-$C_3H_7$ | $C_2H_5$ | H | |
| 113 | isopropylthiocarbonyl | H | n-$C_3H_7$ | $CH_2-CH=CH_2$ | H | |
| 114 | isopropylthiocarbonyl | H | $C_2H_5$ | $CH_2-CH=CH_2$ | H | |
| 115 | isopropylthiocarbonyl | H | $C_2H_5$ | $C_2H_5$ | H | 100–102 |
| 116 | N,N-dimethylcarbamoyl | H | n-$C_3H_7$ | $C_2H_5$ | H | 116–123 |
| 117 | N,N-dimethylcarbamoyl | H | n-$C_3H_7$ | $CH_2-CH=CH_2$ | H | |
| 118 | N,N-dimethylcarbamoyl | H | $C_2H_5$ | $CH_2-CH=CH_2$ | H | |
| 119 | N,N-dimethylcarbamoyl | H | $C_2H_5$ | $C_2H_5$ | H | |
| 120 | N,N-di-n-butylcarbamoyl | H | n-$C_3H_7$ | $C_2H_5$ | H | 175–180 |
| 121 | N,N-di-n-butylcarbamoyl | H | n-$C_3H_7$ | $CH_2-CH=CH_2$ | H | |
| 122 | N,N-di-n-butylcarbamoyl | H | $C_2H_5$ | $CH_2-CH=CH_2$ | H | |
| 123 | N,N-di-n-butylcarbamoyl | H | $C_2H_5$ | $C_2H_5$ | H | |
| 124 | N-methylcarbamoyl | H | n-$C_3H_7$ | $C_2H_5$ | H | 76–78 |
| 125 | N-methylcarbamoyl | H | n-$C_3H_7$ | $CH_2CH=CH_2$ | H | |
| 126 | N-methylcarbamoyl | H | $C_2H_5$ | $CH_2-CH=CH_2$ | H | |
| 127 | N-methylcarbamoyl | H | $C_2H_5$ | $C_2H_5$ | H | |
| 128 | N-n-propylcarbamoyl | H | n-$C_3H_7$ | $C_2H_5$ | H | 114–116 |
| 129 | N-n-propylcarbamoyl | H | n-$C_3H_7$ | $CH_2-CH=CH_2$ | H | |
| 130 | N-n-propylcarbamoyl | H | $C_2H_5$ | $CH_2-CH=CH_2$ | H | |
| 131 | N-n-propylcarbamoyl | H | $C_2H_5$ | $C_2H_5$ | H | |
| 132 | N-cyclohexylcarbamoyl | H | n-$C_3H_7$ | $C_2H_5$ | H | |
| 133 | N-cyclohexylcarbamoyl | H | n-$C_3H_7$ | $CH_2-CH=CH_2$ | H | |
| 134 | N-cyclohexylcarbamoyl | H | $C_2H_5$ | $CH_2CH=CH_2$ | H | |
| 135 | N-cyclohexylcarbamoyl | H | $C_2H_5$ | $C_2H_5$ | H | 140 (decomp.) |
| 136 | N-cyclopentylcarbamoyl | H | n-$C_3H_7$ | $C_2H_5$ | H | 60–62 |
| 137 | N-cyclopentylcarbamoyl | H | n-$C_3H_7$ | $CH_2-CH=CH_2$ | H | |
| 138 | N-cyclooctylcarbamoyl | H | n-$C_3H_7$ | $C_2H_5$ | H | 69–71 |
| 139 | phenylcarbamoyl | H | n-$C_3H_7$ | $C_2H_5$ | H | |
| 140 | phenylcarbamoyl | H | n-$C_3H_7$ | $CH_2-CH=CH_2$ | H | |
| 141 | phenylcarbamoyl | H | $C_2H_5$ | $CH_2-CH=CH_2$ | H | |
| 142 | phenylcarbamoyl | H | $C_2H_5$ | $C_2H_5$ | H | 72–75 |
| 143 | 4-nitrophenylcarbamoyl | H | n-$C_3H_7$ | $C_2H_5$ | H | |
| 144 | 4-nitrophenylcarbamoyl | H | n-$C_3H_7$ | $CH_2-CH=CH_2$ | H | |
| 145 | 3-methoxyphenylcarbamoyl | H | n-$C_3H_7$ | $C_2H_5$ | H | 94–96 |
| 146 | 3-methoxyphenylcarbamoyl | H | n-$C_3H_7$ | $CH_2-CH=CH_2$ | H | |
| 147 | 2-chlorophenylcarbamoyl | H | n-$C_3H_7$ | $C_2H_5$ | H | 84–86 |
| 148 | 2-chlorophenylcarbamoyl | H | n-$C_3H_7$ | $CH_2CH=CH_2$ | H | |
| 149 | 3-methylphenylcarbamoyl | H | n-$C_3H_7$ | $C_2H_5$ | H | 97–98 |
| 150 | 3-methylphenylcarbamoyl | H | n-$C_3H_7$ | $CH_2-CH=CH_2$ | H | |
| 151 | 4-tert.-butylphenylcarbamoyl | H | n-$C_3H_7$ | $C_2H_5$ | H | |
| 152 | 4-n-propoxyphenylcarbamoyl | H | n-$C_3H_7$ | $C_2H_5$ | H | |
| 153 | N-methoxy-N-methylcarbamoyl | H | n-$C_3H_7$ | $C_2H_5$ | H | |
| 154 | N-methoxy-N-methylcarbamoyl | H | n-$C_3H_7$ | $CH_2-CH=CH_2$ | H | |
| 155 | N-methoxy-N-methylcarbamoyl | H | $C_2H_5$ | $CH_2-CH=CH_2$ | H | |
| 156 | N-methoxy-N-methylcarbamoyl | H | $C_2H_5$ | $C_2H_5$ | H | |
| 157 | N-methoxy-N-isopropylcarbamoyl | H | n-$C_3H_7$ | $C_2H_5$ | H | |
| 158 | N-methoxy-N-isopropylcarbamoyl | H | n-$C_3H_7$ | $CH_2-CH=CH_2$ | H | |
| 159 | N-methoxy-N-isopropylcarbamoyl | H | $C_2H_5$ | n-$C_3H_7$ | H | |
| 160 | N-methoxy-N-isopropylcarbamoyl | H | $C_2H_5$ | $C_2H_5$ | H | 118–125 |
| 161 | N-methylsulfamoyl | H | n-$C_3H_7$ | $C_2H_5$ | H | |
| 162 | N-methylsulfamoyl | H | n-$C_3H_7$ | $CH_2-CH=CH_2$ | H | |
| 163 | N-methylsulfamoyl | H | $C_2H_5$ | $CH_2-CH=CH_2$ | | |
| 164 | N-methylsulfamoyl | H | $C_2H_5$ | $C_2H_5$ | H | |
| 165 | N-ethylsulfamoyl | H | n-$C_3H_7$ | $C_2H_5$ | H | |
| 166 | N-ethylsulfamoyl | H | n-$C_3H_7$ | $CH_2-CH=CH_2$ | H | |
| 167 | N-ethylsulfamoyl | H | $C_2H_5$ | $CH_2-CH=CH_2$ | H | |
| 168 | N-ethylsulfamoyl | H | $C_2H_5$ | $C_2H_5$ | H | |
| 169 | N-isobutylsulfamoyl | H | n-$C_3H_7$ | $C_2H_5$ | H | |
| 170 | N-isobutylsulfamoyl | H | n-$C_3H_7$ | $CH_2-CH=CH_2$ | H | |
| 171 | N-isobutylsulfamoyl | H | $C_2H_5$ | $CH_2-CH=CH_2$ | H | |

-continued

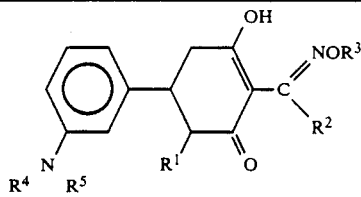

| Compound no. | R⁵ | R¹ | R² | R³ | R⁴ | $n_D$/m.p. [°C.] |
|---|---|---|---|---|---|---|
| 172 | N-isobutylsulfamoyl | H | C₂H₅ | C₂H₅ | H | |
| 173 | N,N-dimethylsulfamoyl | H | n-C₃H₇ | C₂H₅ | H | |
| 174 | N,N-dimethylsulfamoyl | H | n-C₃H₇ | CH₂—CH=CH₂ | H | |
| 175 | N,N-dimethylsulfamoyl | H | C₂H₅ | CH₂—CH=CH₂ | H | |
| 176 | N,N-dimethylsulfamoyl | H | C₂H₅ | C₂H₅ | H | |
| 177 | N,N-diethylsulfamoyl | H | n-C₃H₇ | C₂H₅ | H | |
| 178 | N,N-diethylsulfamoyl | H | n-C₃H₇ | CH₂—CH=CH₂ | H | |
| 179 | N,N-diethylsulfamoyl | H | C₂H₅ | CH₂—CH=CH₂ | H | |
| 180 | N,N-diethylsulfamoyl | H | C₂H₅ | C₂H₅ | H | |
| 181 | N-acetyl-N-methylsulfamoyl | H | n-C₃H₇ | C₂H₅ | H | |
| 182 | N-acetyl-N-methylsulfamoyl | H | n-C₃H₇ | CH₂—CH=CH₂ | H | |
| 183 | N-acetyl-N-methylsulfamoyl | H | C₂H₅ | CH₂—CH=CH₂ | H | |
| 184 | N-acetyl-N-methylsulfamoyl | H | C₂H₅ | C₂H₅ | H | |
| 185 | N-acetyl-N-isopropylsulfamoyl | H | n-C₃H₇ | C₂H₅ | H | |
| 186 | N-acetyl-N-isopropylsulfamoyl | H | n-C₃H₇ | CH₂—CH=CH₂ | H | |
| 187 | N-acetyl-N-isopropylsulfamoyl | H | C₂H₅ | CH₂—CH=CH₂ | H | |
| 188 | N-acetyl-N-isopropylsulfamoyl | H | C₂H₅ | C₂H₅ | H | |
| 189 | N-acetyl-N-n-butylsulfamoyl | H | n-C₃H₇ | C₂H₅ | H | |
| 190 | N-acetyl-N-n-butylsulfamoyl | H | n-C₃H₇ | CH₂—CH=CH₂ | H | |
| 191 | N-acetyl-N-n-butylsulfamoyl | H | C₂H₅ | CH₂—CH=CH₂ | H | |
| 192 | N-acetyl-N-n-butylsulfamoyl | H | C₂H₅ | C₂H₅ | H | |
| 193 | N-butyryl-N-ethylsulfamoyl | H | n-C₃H₇ | C₂H₅ | H | |
| 194 | N-butyryl-N-ethylsulfamoyl | H | n-C₃H₇ | CH₂—CH=CH₂ | H | |
| 195 | N-butyryl-N-ethylsulfamoyl | H | C₂H₅ | CH₂—CH=CH₂ | H | |
| 196 | N-butyryl-N-ethylsulfamoyl | H | C₂H₅ | C₂H₅ | H | |
| 197 | N-methoxycarbonyl-N-methylsulfamoyl | H | n-C₃H₇ | C₂H₅ | H | |
| 198 | N-methoxycarbonyl-N-methylsulfamoyl | H | n-C₃H₇ | CH₂—CH=CH₂ | H | |
| 199 | N-methoxycarbonyl-N-methylsulfamoyl | H | C₂H₅ | CH₂—CH=CH₂ | H | |
| 200 | N-methoxycarbonyl-N-methylsulfamoyl | H | C₂H₅ | C₂H₅ | H | |
| 201 | N-ethyl-N-methoxycarbonylsulfamoyl | H | n-C₃H₇ | C₂H₅ | H | |
| 202 | N-ethyl-N-methoxycarbonylsulfamoyl | H | n-C₃H₇ | CH₂—CH=CH₂ | H | |
| 203 | N-ethyl-N-methoxycarbonylsulfamoyl | H | C₂H₅ | CH₂—CH=CH₂ | H | |
| 204 | N-ethyl-N-methoxycarbonylsulfamoyl | H | C₂H₅ | C₂H₅ | H | |
| 205 | N-isopropyl-N-methoxycarbonylsulfamoyl | H | n-C₃H₇ | C₂H₅ | H | |
| 206 | N-isopropyl-N-methoxycarbonylsulfamoyl | H | n-C₃H₇ | CH₂—CH=CH₂ | H | |
| 207 | N-isopropyl-N-methoxycarbonylsulfamoyl | H | C₂H₅ | CH₂—CH=CH₂ | H | |
| 208 | N-isopropyl-N-methoxycarbonylsulfamoyl | H | C₂H₅ | C₂H₅ | H | |
| 209 | N-(n-butyl)-N-methoxycarbonylsulfamoyl | H | n-C₃H₇ | C₂H₅ | H | |
| 210 | N-(n-butyl)-N-methoxycarbonylsulfamoyl | H | n-C₃H₇ | CH₂—CH=CH₂ | H | |
| 211 | N-(n-butyl)-N-methoxycarbonylsulfamoyl | H | C₂H₅ | CH₂—CH=CH₂ | H | |
| 212 | N-(n-butyl)-N-methoxycarbonylsulfamoyl | H | C₂H₅ | C₂H₅ | H | |
| 385 | hexanoyl | H | n-C₃H₇ | C₂H₅ | H | |

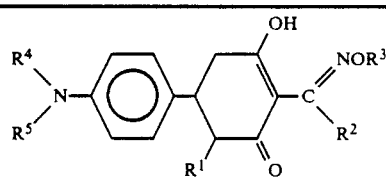

| Compound no. | R⁵ | R¹ | R² | R³ | R⁴ | $n_D$/m.p. [°C.] |
|---|---|---|---|---|---|---|
| 213 | H | H | n-C₃H₇ | C₂H₅ | H | 118 |
| 214 | H | H | C₂H₅ | n-C₃H₇ | H | |
| 215 | H | H | C₂H₅ | CH₂—CH=CH₂ | H | |
| 216 | H | H | n-C₃H₇ | CH₂—CH=CH₂ | H | 92 |
| 217 | H | H | n-C₃H₇ | CH₂—CH=CHCl | H | |
| 218 | methyl | COOCH₃ | n-C₃H₇ | C₂H₅ | CH₃ | 80 |
| 219 | methyl | COOCH₃ | n-C₃H₇ | CH₂—CH=CH₂ | CH₃ | 74 |
| 220 | methyl | H | C₂H₅ | CH₂—CH=CH₂ | CH₃ | |
| 221 | methyl | H | n-C₃H₇ | C₂H₅ | CH₃ | |
| 222 | cyclopropylcarbonyl | H | n-C₃H₇ | C₂H₅ | H | 155-158 |
| 223 | cyclopropylcarbonyl | H | n-C₃H₇ | CH₂—CH=CH₂ | H | |
| 224 | cyclopropylcarbonyl | H | C₂H₅ | CH₂CH=CH₂ | H | |
| 225 | cyclopropylcarbonyl | H | C₂H₅ | C₂H₅ | H | |

-continued

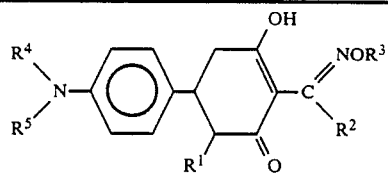

| Compound no. | R⁵ | R¹ | R² | R³ | R⁴ | $n_D$/m.p. [°C.] |
|---|---|---|---|---|---|---|
| 226 | cyclopentylcarbonyl | H | n-$C_3H_7$ | $C_2H_5$ | H | |
| 227 | cyclopentylcarbonyl | H | n-$C_3H_7$ | $CH_2-CH=CH_2$ | H | |
| 228 | cyclopentylcarbonyl | H | $C_2H_5$ | $CH_2-CH=CH_2$ | H | |
| 229 | cyclopentylcarbonyl | H | $C_2H_5$ | $C_2H_5$ | H | |
| 230 | cyclohexylcarbonyl | H | n-$C_3H_7$ | $C_2H_5$ | H | 125–129 |
| 231 | cyclohexylcarbonyl | H | n-$C_3H_7$ | $CH_2-CH=CH_2$ | H | |
| 233 | cyclohexycarbonyl | H | $C_2H_5$ | $C_2H_5$ | H | |
| 234 | methoxyacetyl | H | n-$C_3H_7$ | $C_2H_5$ | H | 131–135 |
| 235 | methoxyacetyl | H | n-$C_3H_7$ | $CH_2-CH=CH_2$ | H | |
| 236 | methoxyacetyl | H | $C_2H_5$ | $CH_2-CH=CH_2$ | H | |
| 237 | methoxyacetyl | H | $C_2H_5$ | $C_2H_5$ | H | |
| 238 | 2-methoxypropionyl | H | n-$C_3H_7$ | $C_2H_5$ | H | 105–108 |
| 239 | 2-methoxypropionyl | H | n-$C_3H_7$ | $CH_2-CH=CH_2$ | H | |
| 240 | 2-methoxypropionyl | H | $C_2H_5$ | $CH_2-CH=CH_2$ | H | |
| 241 | 2-methoxypropionyl | H | $C_2H_5$ | $C_2H_5$ | H | |
| 242 | 3-methoxypropionyl | H | n-$C_3H_7$ | $C_2H_5$ | H | 120–122 |
| 243 | 3-methoxypropionyl | H | n-$C_3H_7$ | $CH_2-CH=CH_2$ | H | |
| 244 | 3-methoxypropionyl | H | $C_2H_5$ | $CH_2-CH=CH_2$ | H | |
| 245 | 3-methoxypropionyl | H | $C_2H_5$ | $C_2H_5$ | H | |
| 246 | benzoyl | H | n-$C_3H_7$ | $C_2H_5$ | H | 161–164 |
| 247 | benzoyl | H | n-$C_3H_7$ | $CH_2-CH=CH_2$ | H | 134–135 |
| 248 | benzoyl | H | $C_2H_5$ | $CH_2-CH=CH_2$ | H | |
| 249 | benzoyl | H | $C_2H_5$ | $C_2H_5$ | H | 147 |
| 250 | 3-nitrobenzoyl | H | n-$C_3H_7$ | $C_2H_5$ | H | 80–81 |
| 251 | 3-nitrobenzoyl | H | n-$C_3H_7$ | $CH_2CH=CH_2$ | H | |
| 252 | 3-nitrobenzoyl | H | $C_2H_5$ | $CH_2-CH=CH_2$ | H | |
| 253 | 3-nitrobenzoyl | H | $C_2H_5$ | $C_2H_5$ | H | |
| 254 | 2-chlorobenzoyl | H | n-$C_3H_7$ | $C_2H_5$ | H | 98–101 |
| 255 | 2-chlorobenzoyl | H | n-$C_3H_7$ | $CH_2-CH=CH_2$ | H | |
| 256 | 3-methoxybenzoyl | H | n-$C_3H_7$ | $C_2H_5$ | H | |
| 257 | 3-methoxybenzoyl | H | n-$C_3H_7$ | $CH_2-CH=CH_2$ | H | |
| 258 | 3-methoxybenzoyl | H | $C_2H_5$ | $CH_2-CH=CH_2$ | H | |
| 259 | 3-methoxybenzoyl | H | $C_2H_5$ | $C_2H_5$ | H | |
| 260 | 4-n-propoxybenzoyl | H | n-$C_3H_7$ | $C_2H_5$ | H | |
| 261 | 4-t-butylbenzoyl | H | n-$C_3H_7$ | $C_2H_5$ | H | 78–79 |
| 262 | 4-nitrobenzoyl | H | n-$C_3H_7$ | $C_2H_5$ | H | 138–141 |
| 263 | 4-nitrobenzoyl | H | n-$C_3H_7$ | $CH_2CH=CH_2$ | H | |
| 264 | 4-nitrobenzoyl | H | $C_2H_5$ | $CH_2-CH=CH_2$ | H | |
| 265 | 4-nitrobenzoyl | H | $C_2H_5$ | $C_2H_5$ | H | |
| 266 | 4-chlorobenzoyl | H | n-$C_3H_7$ | $C_2H_5$ | H | 174–182 |
| 267 | 4-chlorobenzoyl | H | n-$C_3H_7$ | $CH_2-CH=CH_2$ | H | |
| 268 | 4-chlorobenzoyl | H | $C_2H_5$ | $CH_2-CH=CH_2$ | H | |
| 269 | 4-chlorobenzoyl | H | $C_2H_5$ | $C_2H_5$ | H | |
| 270 | 4-methoxybenzoyl | H | n-$C_3H_7$ | $C_2H_5$ | H | |
| 271 | 4-methoxybenzoyl | H | n-$C_3H_7$ | $CH_2-CH=CH_2$ | H | 145–153 |
| 272 | 4-methoxybenzoyl | H | $C_2H_5$ | $CH_2-CH=CH_2$ | H | |
| 273 | 4-methoxybenzoyl | H | $C_2H_5$ | $C_2H_5$ | H | |
| 274 | benzyloxycarbonyl | H | n-$C_3H_7$ | $C_2H_5$ | H | 107–110 |
| 275 | benzyloxycarbonyl | H | n-$C_3H_7$ | $CH_2-CH=CH_2$ | H | |
| 276 | benzyloxycarbonyl | H | $C_2H_5$ | $CH_2CH=CH_2$ | H | |
| 277 | benzyloxycarbonyl | H | $C_2H_5$ | $C_2H_5$ | H | |
| 278 | phenoxycarbonyl | H | n-$C_3H_7$ | $C_2H_5$ | H | 141–146 |
| 279 | phenoxycarbonyl | H | n-$C_3H_7$ | $CH_2-CH=CH_2$ | H | |
| 280 | phenoxycarbonyl | H | $C_2H_5$ | $CH_2-CH=CH_2$ | H | |
| 281 | phenoxycarbonyl | H | $C_2H_5$ | $C_2H_5$ | H | |
| 282 | methylthiocarbonyl | H | n-$C_3H_7$ | $C_2H_5$ | H | 165–166 |
| 283 | methylthiocarbonyl | H | n-$C_3H_7$ | $CH_2-CH=CH_2$ | H | |
| 284 | methylthiocarbonyl | H | $C_2H_5$ | $CH_2-CH=CH_2$ | H | |
| 285 | methylthiocarbonyl | H | $C_2H_5$ | $C_2H_5$ | H | |
| 286 | ethylthiocarbonyl | H | n-$C_3H_7$ | $C_2H_5$ | H | |
| 287 | ethylthiocarbonyl | H | n-$C_3H_7$ | $CH_2-CH=CH_2$ | H | |
| 288 | ethylthiocarbonyl | H | $C_2H_5$ | $CH_2-CH=CH_2$ | H | |
| 289 | ethylthiocarbonyl | H | $C_2H_5$ | $C_2H_5$ | H | |
| 290 | isopropylthiocarbonyl | H | n-$C_3H_7$ | $C_2H_5$ | H | |
| 291 | isopropylthiocarbonyl | H | n-$C_3H_7$ | $CH_2-CH=CH_2$ | H | |
| 292 | isopropylthiocarbonyl | H | $C_2H_5$ | $CH_2-CH=CH_2$ | H | |
| 293 | isopropylthiocarbonyl | H | $C_2H_5$ | $C_2H_5$ | H | |
| 294 | N-cyclohexylcarbamoyl | H | n-$C_3H_7$ | $C_2H_5$ | H | 92–95 |
| 295 | N-cyclohexylcarbamoyl | H | n-$C_3H_7$ | $CH_2-CH=CH_2$ | H | |
| 296 | N-cyclohexylcarbamoyl | H | $C_2H_5$ | $CH_2-CH=CH_2$ | H | |
| 297 | N-cyclohexylcarbamoyl | H | $C_2H_5$ | $C_2H_5$ | H | |

-continued

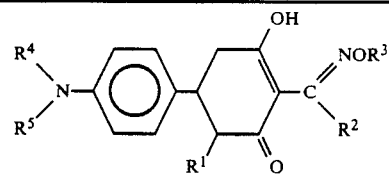

| Compound no. | R⁵ | R¹ | R² | R³ | R⁴ | $n_D$/m.p. [°C.] |
|---|---|---|---|---|---|---|
| 298 | N-cyclopentylcarbamoyl | H | n-C₃H₇ | C₂H₅ | H | |
| 299 | N-cyclopentylcarbamoyl | H | n-C₃H₇ | n-C₃H₇ | H | 92–95 |
| 300 | N-cyclooctylcarbamoyl | H | n-C₃H₇ | n-C₃H₇ | H | 75–78 |
| 301 | phenylcarbamoyl | H | n-C₃H₇ | C₂H₅ | H | 152–153 |
| 302 | phenylcarbamoyl | H | n-C₃H₇ | CH₂—CH=CH₂ | H | 78–81 |
| 303 | phenylcarbamoyl | H | C₂H₅ | CH₂—CH=CH₂ | H | |
| 304 | phenylcarbamoyl | H | C₂H₅ | C₂H₅ | H | |
| 305 | 4-nitrophenylcarbamoyl | H | n-C₃H₇ | C₂H₅ | H | |
| 306 | 4-nitrophenylcarbamoyl | H | n-C₃H₇ | CH₂—CH=CH₂ | H | |
| 307 | 3-methoxyphenylcarbamoyl | H | n-C₃H₇ | C₂H₅ | H | 158–160 |
| 308 | 3-methoxyphenylcarbamoyl | H | n-C₃H₇ | CH₂—CH=CH₂ | H | |
| 309 | 2-chlorophenylcarbamoyl | H | n-C₃H₇ | C₂H₅ | H | 77–80 |
| 310 | 2-chlorophenylcarbamoyl | H | n-C₃H₇ | CH₂CH=CH₂ | H | |
| 311 | 3-methylphenylcarbamoyl | H | n-C₃H₇ | C₂H₅ | H | 164–166 |
| 312 | 3-methylphenylcarbamoyl | H | n-C₃H₇ | CH₂—CH=CH₂ | H | |
| 313 | 4-tert.-butylphenyl(carbamoyl) | H | n-C₃H₇ | C₂H₅ | H | |
| 314 | 4-n-propoxyphenylcarbamoyl | H | n-C₃H₇ | C₂H₅ | H | |
| 315 | N-methylsulfamoyl | H | n-C₃H₇ | C₂H₅ | H | 151–156 |
| 316 | N-methylsulfamoyl | H | n-C₃H₇ | CH₂—CH=CH₂ | H | |
| 317 | N-methylsulfamoyl | H | C₂H₅ | CH₂—CH=CH₂ | H | |
| 318 | N-methylsulfamoyl | H | C₂H₅ | C₂H₅ | H | |
| 319 | N-ethylsulfamoyl | H | n-C₃H₇ | C₂H₅ | H | |
| 320 | N-ethylsulfamoyl | H | n-C₃H₇ | CH₂—CH=CH₂ | H | |
| 321 | N-ethylsulfamoyl | H | C₂H₅ | CH₂—CH=CH₂ | H | |
| 322 | N-ethylsulfamoyl | H | C₂H₅ | C₂H₅ | H | |
| 323 | N-isobutylsulfamoyl | H | n-C₃H₇ | C₂H₅ | H | |
| 324 | N-isobutylsulfamoyl | H | n-C₃H₇ | CH₂—CH=CH₂ | H | |
| 325 | N-isobutylsulfamoyl | H | C₂H₅ | CH₂—CH=CH₂ | H | |
| 326 | N-isobutylsulfamoyl | H | C₂H₅ | C₂H₅ | H | |
| 327 | N,N-dimethylsulfamoyl | H | n-C₃H₇ | C₂H₅ | H | |
| 328 | N,N-dimethylsulfamoyl | H | n-C₃H₇ | CH₂—CH=CH₂ | H | |
| 329 | N,N-dimethylsulfamoyl | H | C₂H₅ | CH₂—CH=CH₂ | H | |
| 330 | N,N-dimethylsulfamoyl | H | C₂H₅ | C₂H₅ | H | |
| 331 | N,N-diethylsulfamoyl | H | n-C₃H₇ | C₂H₅ | H | |
| 332 | N,N-diethylsulfamoyl | H | n-C₃H₇ | CH₂—CH=CH₂ | H | |
| 333 | N,N-diethylsulfamoyl | H | C₂H₅ | CH₂—CH=CH₂ | H | |
| 334 | N,N-diethylsulfamoyl | H | C₂H₅ | C₂H₅ | H | |
| 335 | N-acetyl-N-methylsulfamoyl | H | n-C₃H₇ | C₂H₅ | H | |
| 336 | N-acetyl-N-methylsulfamoyl | H | n-C₃H₇ | CH₂—CH=CH₂ | H | |
| 337 | N-acetyl-N-methylsulfamoyl | H | C₂H₅ | CH₂—CH=CH₂ | H | |
| 338 | N-acetyl-N-methylsulfamoyl | H | C₂H₅ | C₂H₅ | H | |
| 339 | N-acetyl-N-isopropylsulfamoyl | H | n-C₃H₇ | C₂H₅ | H | |
| 340 | N-acetyl-N-isopropylsulfamoyl | H | n-C₃H₇ | CH₂—CH=CH₂ | H | |
| 341 | N-acetyl-N-isopropylsulfamoyl | H | C₂H₅ | CH₂—CH=CH₂ | H | |
| 342 | N-acetyl-N-isopropylsulfamoyl | H | C₂H₅ | C₂H₅ | H | |
| 343 | N-acetyl-N-n-butylsulfamoyl | H | n-C₃H₇ | C₂H₅ | H | |
| 344 | N-acetyl-N-n-butylsulfamoyl | H | n-C₃H₇ | CH₂—CH=CH₂ | H | |
| 345 | N-acetyl-N-n-butylsulfamoyl | H | C₂H₅ | CH₂—CH=CH₂ | H | |
| 346 | N-acetyl-N-n-butylsulfamoyl | H | C₂H₅ | C₂H₅ | H | |
| 347 | N-nutyryl-N-ethylsulfamoyl | H | n-C₃H₇ | C₂H₅ | H | |
| 348 | N-butyryl-N-ethylsulfamoyl | H | n-C₃H₇ | CH₂—CH=CH₂ | H | |
| 349 | N-butyryl-N-ethylsulfamoyl | H | C₂H₅ | CH₂—CH=CH₂ | H | |
| 350 | N-butyryl-N-ethylsulfamoyl | H | C₂H₅ | C₂H₅ | H | |
| 351 | N-methoxycarbonyl-N-methylsulfamoyl | H | n-C₃H₇ | C₂H₅ | H | |
| 352 | N-methoxycarbonyl-N-methylsulfamoyl | H | n-C₃H₇ | CH₂—CH=CH₂ | H | |
| 353 | N-methoxycarbonyl-N-methylsulfamoyl | H | C₂H₅ | CH₂—CH=CH₂ | H | |
| 354 | N-methoxycarbonyl-N-methylsulfamoyl | H | C₂H₅ | C₂H₅ | H | |
| 355 | N-ethyl-N-methoxycarbonylsulfamoyl | H | n-C₃H₇ | C₂H₅ | H | |
| 356 | N-ethyl-N-methoxycarbonylsulfamoyl | H | n-C₃H₇ | CH₂—CH=CH₂ | H | |
| 357 | N-ethyl-N-methoxycarbonylsulfamoyl | H | C₂H₅ | CH₂—CH=CH₂ | H | |
| 358 | N-ethyl-N-methoxycarbonylsulfamoyl | H | C₂H₅ | C₂H₅ | H | |
| 359 | N-isopropyl-N-methoxycarbonylsulfamoyl | H | n-C₃H₇ | C₂H₅ | H | |
| 360 | N-isopropyl-N-methoxycarbonylsulfamoyl | H | n-C₃H₇ | CH₂—CH=CH₂ | H | |
| 361 | N-isopropyl-N-methoxycarbonylsulfamoyl | H | C₂H₅ | CH₂CH=CH₂ | H | |
| 362 | N-isopropyl-N-methoxycarbonylsulfamoyl | H | C₂H₅ | C₂H₅ | H | |
| 363 | N-(n-butyl)-N-methoxycarbonylsulfamoyl | H | n-C₃H₇ | C₂H₅ | H | |
| 364 | N-(n-butyl)-N-methoxycarbonylsulfamoyl | H | n-C₃H₇ | CH₂—CH=CH₂ | H | |
| 365 | N-(n-butyl)-N-methoxycarbonylsulfamoyl | H | C₂H₅ | CH₂—CH=CH₂ | H | |
| 366 | N-(n-butyl)-N-methoxycarbonylsulfamoyl | H | C₂H₅ | C₂H₅ | H | |
| 367 | benzoyl | H | n-C₃H₇ | n-C₃H₇ | H | 59 |
| 368 | benzoyl | H | n-C₃H₇ | CH₂—CH=CH—Cl | H | 124–125 |

-continued

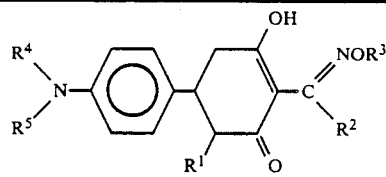

| Compound no. | R⁵ | R¹ | R² | R³ | R⁴ | $n_D$/m.p. [°C.] |
|---|---|---|---|---|---|---|
| 369 | benzoyl | H | n-C₃H₇ | CH₂—C≡CH | H | 126–127 |
| 370 | benzoyl | H | n-C₃H₇ | CH₂—CCl=CCl₂ | H | |
| 371 | benzoyl | H | C₂H₅ | n-C₃H₇ | H | |
| 372 | benzoyl | H | C₂H₅ | CH₂—CH=CH—Cl | H | |
| 373 | benzoyl | H | C₂H₅ | CH₂—C≡CH | H | |
| 374 | CH₃ | H | n-C₃H₇ | allyl | CH₃ | |
| 375 | C₂H₅ | H | n-C₃H₇ | allyl | C₂H₅ | 1,5663 (27) |
| 376 | C₂H₅ | H | n-C₃H₇ | C₂H₅ | C₂H₅ | 1,5617 (27) |
| 377 | 2,4,6-trimethyl-benzoyl | H | n-C₃H₇ | C₂H₅ | H | 100–105 |
| 378 | 3,5-dichloro-benzoyl | H | n-C₃H₇ | C₂H₅ | H | 123–130 |
| 379 | 2-fluoro-benzoyl | H | C₂H₅ | C₂H₅ | H | 133–135 |
| 380 | 4-fluoro-benzoyl | H | C₂H₅ | C₂H₅ | H | 193–195 |
| 381 | 2-iodo-benzoyl | H | C₂H₅ | C₂H₅ | H | 148 |
| 382 | 2,6-dichloro-benzoyl | H | C₂H₅ | C₂H₅ | H | 178–180 |
| 384 | n-propylthiocarbonyl | H | C₂H₅ | C₂H₅ | H | |
| 386 | benzoyl | H | n-C₃H₇ | C₂H₅ | H | sodium salt >200 |
| 387 | benzoyl | H | n-C₃H₇ | C₂H₅ | H | potassium salt >200 |
| 388 | benzoyl | H | n-C₃H₇ | C₂H₅ | H | barium salt 190 (decomp.) |
| 389 | benzoyl | H | n-C₃H₇ | C₂H₅ | H | copper salt 190–200 |
| 390 | benzoyl | H | n-C₃H₇ | C₂H₅ | H | triethylbenzyl-ammonium salt 116–120 |

¹H-NMR-spectroscopic data:

Chemical shift in δ values [ppm] in CDCl₃, based on tetramethylsilane as internal standard (s=singlet, d=doublet, t=triplet, q=quartet, m=multiplet)

| Compound no. | Characteristic signals |
|---|---|
| 1 | 0.98 (t, 3H); 1,22 (t, 3H); 1.59 (q, 2H); 2.73 (s, 4H); 2.96 (t, 2H); 3.25 (m, 1H), 4.12 (q, 2H); 6.62 (m, 3H); 7.14 (t, 1H) |
| 14 | 0.98 (t, 3H); 1.23 (t, 3H); 1.32 (t, 3H); 2.40 (q, 2H) |
| 18 | 0.96 (t, 3H); 1.15 (t, 3H); 1.32 (t, 3H); 2.35 (q, 2H); 6.94 (d, 1H); 7.23 (dd, 1H) |
| 26 | 7.03 (m), 7.41 (m), 8.17 (m), 8.4 (s), 8.72 (d); 6 H-atoms |
| 31 | 0.6–2.0 (m, 13 H); 4.10 (q, 2H) |
| 46 | 3.52 (s, 3H); 4.01 (s, 2H); 7.02 (d, 1H); 7.32 (dd, 1H); 7.46 (d, 1H); 7.56 (s, 1H) |
| 50 | 1.17 (t, 3H); 1.33 (t, 3H); 1.48 (d, 3H); 3.49 (s, 3H); 3.89 (q, 1H) |
| 51 | 3.37 (s, 3H); 3.67 (t, 2H); 4.07 (q, 2H) |
| 58 | 7.01 (m, 1H); 7.16 (t, 1H); 7.23 (m, 4H); 7.31 (s, 1H); 7.94 (d, 2H) |
| 91 | 0.96 (t, 3H); 1.30 (m, 6H); 4.11 (q, 2H); 4.20 (q, 2H) |
| 95 | 9.6–2.0 (m, 15 H); 4.10 (m, 4H) |
| 99 | 4.12 (q, 2H); 5.10 (s, 2H); 6.95 (m, 2H); 7.27 (m, 2H); 7.37 (m, 5H) |
| 153 | 3.13 (s, 3H); 3.71 (s, 3H); 4.08 (q, 2H) |
| 156 | 1.21 (d, 6H); 3.83 (s, 3H); 4.17 (q, 2H); 4.44 (m, 1H) |
| 157 | 1.17 (d, 6H); 3.73 (s, 3H); 4.05 (m, 4H) |
| 159 | 1.21 (d, 6H); 2.96 (m, 2H); 3.79 (s, 3H); 4.02 (t, 2H); 4.43 (m, 1H) |
| 164 | 2.71 (CH₃N); 2.98 (q, 2H); 4.98 (NH); 6.98 (d, 1H); 7.12 (m, 2H); 7.37 (d, 1H) |
| 176 | 1.17 (t, 3H); 1.34 (t, 3H); 2.86 (s, CH₃N), 3.34 (m, 1H); 4.15 (q, 2H) |
| 180 | 1.0–1,5 (m, 12H); 3.30 (q, 4H); 4.16 (q, 2H), 7.05 (m, 3H); 7.28 (m, 1H) |
| 213 | 0.97 (t, 3H); 1.31 (t, 3H); 1.58 (m, 2H); 2.7 (4H); 2.94 (t, 2H); 3.23 (m, 1H); 4.12 (q, 2H); 6.67 (d, 2H); 7.02 (d, 2H) |
| 246 | 0.98 (t, 3H); 1.33 (t, 3H); 1.58 (m, 2H); 2.74 (4H); 2.96 (t, 2H); 3.33 (m, 1H); 4.12 (q, 2H); 7.24 (d, 2H); 7.51 (m, 3H); 7.63 (d, 2H); 7.87 (d, 2H); 7.91 (s,.NH) |
| 247 | 0.97 (t, 3H); 1.61 (m, 2H); 4.57 (d, 2H); 5.3–5.5 (2H); 5.99 (m, 1H) |
| 249 | 1.13 (t, 3H); 1.30 (t, 3H); 7.13 (d, 2H); 7.45 (m, 3H); 7.57 (d, 2H); 7.81 (m, 2H) |
| 282 | 2.42 (s, 3H); 4.10 (q, 2H); 7.18 (d, 2H); 7.32 (s, NH); 7.42 (d, 2H) |
| 315 | 0.97 (t, 3H); 1.33 (t, 3H); 2.73 (s, CH₃N); 4.85 (NH); 7.18 (s, 4H) |
| 327 | 2.84 (s, 6H, CH₃N); 4.12 (q, 2H); 7.18 (s, 4H) |
| 330 | 1.17 (t, 3H); 1.33 (t, 3H); 2.83 (s, CH₃N); 3.22 (m, 1H); 4.15 (q, 2H); 7.19 (s, 4H) |
| 331 | 0.97 (t, 3H); 1.07 (t, 6H); 1.33 (t, 3H); 3.27 (q, 4H); 4.11 (q, 2H); 7.15 (s, 4H) |
| 368 | 0.97 (t, 3H); 1.56 (q, 2H); 3.32 (m, 1H); 4.54, 4.78 (d, d, 2H); 6.05 (m, 1H); 6.34 (m, 1H) |
| 369 | 4.67 (s, 2H); 7.21 (d, 2H); 7.50 (m, 3H), 7.62 (d, 2H); 7.87 (d, 2H); 8.12 (s, NH) |
| 374 | 2.85 (s, 6H); 4.50 (d, 2H); 6.70 (d, 2H); 7.15 (d, 2H) |

The cyclohexenone derivatives of the formula I and their salts, or herbicidal agents containing them, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, and N-methylpyrrolidone and water are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

Examples of formulations are given below.

I. 90 parts by weight of compound no. 2 is mixed with 10 parts by weight of N-methyl-alpha-pyrrolidone. A mixture is obtained which is suitable for application in the form of very fine drops.

II. 20 parts by weight of compound no. 3 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 1 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 17 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 12 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 52 is intimately mixed with 97 parts by weight of particulate kaolin. A dust is obtained containing 3% by weight of the active ingredient.

VII. 30 parts by weight of compound no. 53 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of compound no. 14 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients may be applied pre- or post-emergence. If certain crop plants tolerate the active ingredients less well when they are applied postemergence; application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The amount of active ingredient applied depends on the time of the year, the plants to be combated and their growth stage, and varies from 0.025 to 3 kg/ha and more, but is preferably from 0.1 to 0.5 kg/ha.

The herbicidal action of the cyclohexenone derivatives of the formula I is demonstrated in greenhouse experiments.

The vessels employed were plastic flowerpots having a volume of 300 cm³, and which were filled with a sand loam containing about 3% humus. The seeds of the test plants were sown shallow, and separately, according to species. For the preemergence treatment, the active ingredients were applied to the surface of the soil immediately after the seeds had been sown. The compounds were emulsified or suspended in water as vehicle, and sprayed through finely distributing nozzles. The application rate was 3.0 kg of active ingredient per hectare. After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, the plants were first grown in the vessels to a height of from 3 to 15 cm, depending on growth form, before being treated. The soybean plants were grown in a peat-enriched substrate. For this treatment, either plants which had been sown directly in the pots and grown there were selected, or plants which had been grown from seedlings and were transplanted to the pots a few days before treatment. The application rates for postemergence treatment were 0.25, 0.5, 1.0 and 3.0 kg of active ingredient per hectare.

The pots were set up in the greenhouse-species from warmer areas at from 20° to 35° C., and species from moderate climates at 10° to 25° C. The experiments were run for 3 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The plants used in the experiments were Alopecurus myosuroides, Avena fatua, Brassica napus, Digitaria sanguinalis, Echinochloa crus-galli, Glycine max., Hordeum vulgare, Leptochloa fascicularis, Lolium multiflorum, Oryza sativa, Setaria faberii, Setaria italica, Sinapis alba, Sorghum halepense, Triticum aestivum and Zea mays.

The agents used for comparison purposes were the compounds of the formula

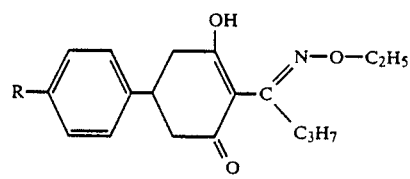

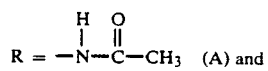 (A) and

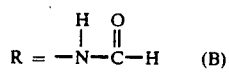 (B)

disclosed in German Laid-Open Application DE-OS No. 3,248,554.

The test results reveal the following directions of action of the cyclohexenone derivatives of the formula I:

(a) activity on plant species from the Gramineae family, combined with excellent tolerance by broadleaved plants;
(b) action on specific unwanted grasses, while at the same time selective in Gramineae crops;
(c) effective on both grassy and broadleaved unwanted plants; and
(d) action on broadleaved weeds, combined with tolerance for grassy crop plants.

Preemergence application

For example compounds nos. 380, 384, 176, 159, 103, 222, 213, 367 and 247 proved to be herbicidally effective on plants from the Gramineae family, while white mustard (Sinapis alba), a dicotyledonous member of the Cruciferae family, remained completely undamaged.

Postemergence application

Compound no. 246, applied at a rate of 0.5 kg/ha, selectively combatted unwanted grassy plants in rice, which is also a member of the Gramineae family. By contrast comparative agent A caused intolerable damage to the rice crop. Compound no. 246 also combatted unwanted grassy without damaging broadleaved crop plants.

Compound nos. 107, 115 and 381, applied for instance at a rate of 0.25 kg/ha, controlled the grassy weed Alopercurus myosuroides selected by way of example, while wheat was ony slightly damaged, if at all. By contrast, comparative agents A and B inflicted heavy damage on the cereal. Compound no. 221, at 1.0 kg/ha, selectively combatted unwanted grasses in barley.

Compounds nos. 128, 116, 153, 157 and 160, at a rate of 1.0 kg/ha, demonstrated for example selectivity in combatting unwanted grasses in Indian corn.

In view of the broad spectrum of weeds which can be combatted, the tolerance by crop plants (or the desired influence on their growth), and the variety of application methods possible, the compounds according to the invention may, depending on the substituents, be used in a large number of crop plants.

The following crops may be mentioned by way of example:

| Botanical name | Common name |
|---|---|
| Allium cepa | onions |
| Ananas comosus | pineapples |
| Arachis hypogaea | peanuts (groundnuts) |
| Asparagus officinalis | asparagus |
| Avena sativa | oats |
| Beta vulgaris spp. altissima | sugarbeets |
| Beta vulgaris spp. rapa | fodder beets |
| Beta vulgaris spp. esculenta | table beets, red beets |
| Brassica napus var. napus | oilseed rape |
| Brassica napus var. napobrassica | swedes |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |

| Botanical name | Common name |
| --- | --- |
| Cynodon dactylon | Bermudagrass in turf and lawns |
| Daucus carota | carrots |
| Eaeis guineensis | oil palms |
| Fragaria vesca | strawberries |
| Glycine max | soybeans |
| Gossypium hirsutum (Gossypium arboreum Gossypium herbaceum Gossypium vitifolium) | cotton |
| Helianthus annuus | sunflowers |
| Helianthus tuberosus | Jerusalem artichoke |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicothiana tabacum (N. rustica) | tobacco |
| Olea europaea | olive trees |
| Oryza sativa | rice |
| Panicum miliaceum | millet |
| Phaseolus lunatus | limabeans |
| Phaseolus mungo | mungbeans |
| Phaseolus vulgaris | snapbeans, green beans, dry beans |
| Pennisetum glaucum | pearl millet |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcia | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna | sorgo |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

To increase the spectrum of action and to achieve synergistic effects, the cyclohexenone derivatives of the formula I, or agents containing them, may be mixed and applied together with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, triazinones, uracils, benzofuran derivatives, cyclohexane-1,3-dione derivatives, etc.

It may also be useful to apply the novel compounds, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

We claim:

1. A cyclohexenone derivative of the formula

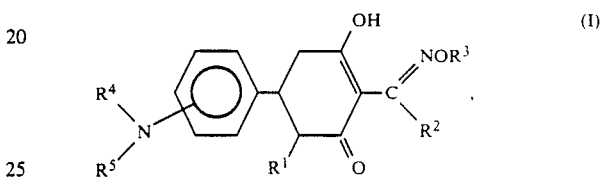

wherein $R^1$ hydrogen, $R^2$ is alkyl of 1 to 4 carbon atoms, $R^3$ is alkyl of 1 to 4 carbon atoms, alkenyl of 3 or 4 carbon atoms, haloalkenyl of 3 or 4 carbon atoms and 1 to 3 halogen substituents, or propargyl, $R^4$ is hydrogen, $R^5$ is formyl, or unsubstituted benzoyl, and, the $-NR^4R^5$ group is in the para-position when $R^5$ is unsubstituted benzoyl and in the meta-position when $R^5$ is formyl.

2. A cyclohexenone derivative of the formula I as defined in claim 1, where $R^5$ is benzoyl.

3. A herbicidal composition containing inert additives and an effective amount of a cyclohexenone derivative of the formula I as defined in claim 1, or a salt thereof.

4. A herbicidal composition as defined in claim 3, containing from 0.1 to 95 wt % of the cyclohexenone derivative of the formula I.

5. A herbicidal composition containing inert additives and an effective amount of a cyclohexenone derivative of the formula I as defined in claim 2, or a salt thereof.

6. A process for controlling the growth of unwanted plants, wherein the unwanted plants and/or the area to be kept free from unwanted plant growth are treated with a herbicidally effective amount of a cyclohexenone derivative of the formula I as defined in claim 1, or a salt thereof.

7. The compound of the formula I as defined in claim 1, wherein $R^1$ is H, $R^2$ is n-propyl, $R^3$ is ethyl, $R^4$ is H and $R^5$ is benzoyl.

8. The herbicidal composition of claim 5, wherein in the compound of the formula I as defined in claim 1, $R^1$ is H, $R^2$ is n-propyl, $R^3$ is ethyl, $R^4$ is H and $R^5$ is benzoyl.

9. The process of claim 6, wherein the compound of the formula I as defined in claim 1, $R^1$ is H, $R^2$ is n-propyl, $R^3$ is ethyl, $R^4$ is H and $R^5$ is benzoyl.

* * * * *